United States Patent
Yang et al.

(10) Patent No.: US 9,014,815 B2
(45) Date of Patent: Apr. 21, 2015

(54) ELECTRODE ASSEMBLY IN A MEDICAL ELECTRICAL LEAD

(75) Inventors: Zhongping C. Yang, Woodbury, MN (US); Piotr J. Przybyszewski, Fremont, CA (US); Ben W. Herberg, Andover, MN (US); Kevin R. Seifert, Forest Lake, MN (US); Dina L. Williams, Andover, MN (US)

(73) Assignee: Medtronic, Inc., Minneapolis, MN (US)

( * ) Notice: Subject to any disclaimer, the term of this patent is extended or adjusted under 35 U.S.C. 154(b) by 967 days.

(21) Appl. No.: 12/915,631

(22) Filed: Oct. 29, 2010

(65) Prior Publication Data

US 2011/0118813 A1    May 19, 2011

Related U.S. Application Data

(60) Provisional application No. 61/262,795, filed on Nov. 19, 2009.

(51) Int. Cl.
*A61N 1/05*    (2006.01)
*A61N 1/375*   (2006.01)
*A61N 1/37*    (2006.01)
*A61N 1/08*    (2006.01)

(52) U.S. Cl.
CPC ............. *A61N 1/375* (2013.01); *A61N 1/3718* (2013.01); *A61N 2001/086* (2013.01); *A61N 1/05* (2013.01)

(58) Field of Classification Search
USPC .................................. 607/115, 116
See application file for complete search history.

(56) References Cited

U.S. PATENT DOCUMENTS 4,917,104 A * 4/1990 Rebell ............................ 600/585
5,445,859 A * 8/1995 Lindegren et al. .............. 428/76
(Continued)

FOREIGN PATENT DOCUMENTS

WO    03037424 A2    5/2003
WO    2008036865 A2    3/2008
(Continued)

OTHER PUBLICATIONS (PCT/US2010/057374) PCT Notification of Transmittal of the International Search Report and the Written Opinion of the International Searching Authority, 11 pages.
(Continued)

*Primary Examiner* — Alyssa M Alter
(74) *Attorney, Agent, or Firm* — Michael J. Ostrom; Stephen W. Bauer

(57) ABSTRACT

A medical device lead is presented that includes an electrode assembly having a first electrode located near a distal end of the electrode assembly and a second electrode located near a proximal end of the electrode assembly. The electrode assembly also includes a conductive elongated coupler that is electrically coupled to the first electrode and capacitively coupled to the second electrode. At low frequencies and DC (e.g., during delivery of stimulation therapy), the capacitive coupling between the conductive elongated coupler and the second electrode presents a high impedance allowing little current to be redirected from the first electrode to the second electrode. However, at high frequencies (e.g., during an MRI scan) the capacitive coupling between the conductive elongated coupler and the second electrode presents a low impedance, resulting in a significant amount of induced current being redirected to the second electrode and dissipated into bodily fluid surrounding the second electrode.

24 Claims, 18 Drawing Sheets

(56) References Cited

U.S. PATENT DOCUMENTS

| | | | |
|---|---|---|---|
| 5,824,030 A * | 10/1998 | Yang et al. | 607/122 |
| 6,944,489 B2 * | 9/2005 | Zeijlemaker et al. | 600/373 |
| 6,985,775 B2 | 1/2006 | Reinke et al. | |
| 7,174,219 B2 | 2/2007 | Wahlstrand et al. | |
| 7,289,856 B1 | 10/2007 | Karicherla | |
| 7,363,090 B2 | 4/2008 | Halperin et al. | |
| 7,689,288 B2 | 3/2010 | Stevenson et al. | |
| 7,751,903 B2 | 7/2010 | Stevenson et al. | |
| 2002/0128691 A1 | 9/2002 | Connelly | |
| 2003/0083723 A1 | 5/2003 | Wilkinson et al. | |
| 2003/0144718 A1 | 7/2003 | Zeijlemaker | |
| 2003/0216800 A1 | 11/2003 | Ebert et al. | |
| 2004/0064024 A1 * | 4/2004 | Sommer | 600/374 |
| 2005/0070972 A1 | 3/2005 | Wahlstrand et al. | |
| 2005/0090886 A1 | 4/2005 | MacDonald et al. | |
| 2005/0159661 A1 | 7/2005 | Connelly et al. | |
| 2005/0222658 A1 | 10/2005 | Hoegh et al. | |
| 2006/0200218 A1 | 9/2006 | Wahlstrand | |
| 2006/0247747 A1 * | 11/2006 | Olsen et al. | 607/116 |
| 2006/0247748 A1 | 11/2006 | Wahlstrand et al. | |
| 2006/0259088 A1 * | 11/2006 | Pastore et al. | 607/9 |
| 2007/0093142 A1 | 4/2007 | MacDonald et al. | |
| 2007/0208383 A1 | 9/2007 | Williams | |
| 2007/0244535 A1 | 10/2007 | Inman et al. | |
| 2007/0299490 A1 | 12/2007 | Yang et al. | |
| 2008/0009905 A1 | 1/2008 | Zeijlemaker | |
| 2008/0116997 A1 | 5/2008 | Dabney et al. | |
| 2008/0132985 A1 | 6/2008 | Wedan et al. | |
| 2008/0147154 A1 | 6/2008 | Gray et al. | |
| 2008/0154346 A1 | 6/2008 | Smith et al. | |
| 2008/0154348 A1 | 6/2008 | Atalar et al. | |
| 2008/0221568 A1 | 9/2008 | Stone | |
| 2008/0269830 A1 | 10/2008 | Marshall | |
| 2008/0269855 A1 | 10/2008 | Marshall | |
| 2008/0281390 A1 | 11/2008 | Marshall | |
| 2009/0149920 A1 | 6/2009 | Li et al. | |
| 2009/0149934 A1 | 6/2009 | Ameri et al. | |
| 2009/0198314 A1 | 8/2009 | Foster et al. | |
| 2009/0240296 A1 | 9/2009 | Zeijlemaker et al. | |
| 2010/0217262 A1 | 8/2010 | Stevenson et al. | |
| 2011/0034979 A1 | 2/2011 | Min et al. | |
| 2011/0040343 A1 | 2/2011 | Johnson et al. | |
| 2011/0071604 A1 | 3/2011 | Wahlstrand et al. | |
| 2011/0270369 A1 | 11/2011 | Tekmen et al. | |

FOREIGN PATENT DOCUMENTS

| | | |
|---|---|---|
| WO | 2008095059 A1 | 8/2008 |
| WO | 2009134901 A1 | 11/2009 |
| WO | 2010/008833 | 1/2010 |

OTHER PUBLICATIONS

Office Action from Related U.S. Appl. No. 13/097,187, dated Sep. 13, 2012, 26 pages.
Response to Office Action from Related U.S. Appl. No. 13/097,187, submitted Dec. 12, 2012, 9 pages.
Final Office Action from Related U.S. Appl. No. 13/097,187, dated Feb. 25, 2013, 12 pages.
Response to Final Office Action from Related U.S. Appl. No. 13/097,187, submitted Apr. 25, 2013, 9 pages.
Advisory Action from Related U.S. Appl. No. 13/097,187, dated May 7, 2013, 5 pages.
Applicant Initiated Interview Summary from Related U.S. Appl. No. 13/097,187, dated May 9, 2013, 3 pages.
Response to Advisory Action with RCE Transmittal from Related U.S. Appl. No. 13/097,187, submitted May 28, 2013, 7 pages.
Office Action from Related U.S. Appl. No. 13/097,187, dated Apr. 24, 2014, 19 pages.
Response to Office Action from Related U.S. Appl. No. 13/097,187, submitted Jul. 23, 2014, 7 pages.
Final Office Action from Related U.S. Appl. No. 13/097,187, dated Aug. 27, 2014, 21 pages.
Response to Final Office Action and After Final Consideration Program Request from Related U.S. Appl. No. 13/097,187, submitted Oct. 27, 2014, 8 pages.
Advisory Action from Related U.S. Appl. No. 13/097,187, dated Nov. 6, 2014, 5 pages.
Request for Continued Examination from Related U.S. Appl. No. 13/097,187, submitted Nov. 10, 2014, 2 pages.
Office Action from Related U.S. Appl. No. 13/097,187, dated Dec. 1, 2014, 17 pages.
Response to Office Action dated Dec. 1, 2014, from U.S. Appl. No. 13/097,187, submitted Mar. 2, 2015, 7 pages.

* cited by examiner

ELECTRODE ASSEMBLY IN A MEDICAL ELECTRICAL LEAD

This application claims the benefit of U.S. Provisional Application No. 61/262,795, filed on Nov. 19, 2009, the content of which is incorporated herein by reference in its entirety.

TECHNICAL FIELD

The present disclosure relates to implantable medical devices (IMD) and, more particularly, to an electrode assembly for redirecting a portion of radio frequency (RF) energy or RF induced current away from a tip electrode in a medical electrical lead.

BACKGROUND

In the medical field, implantable leads are used with a wide variety of medical devices. For example, implantable leads are commonly used to form part of implantable cardiac system that provides therapeutic stimulation to the heart by delivering pacing, cardioversion, defibrillation or resynchronization pulses. The pulses can be delivered to the heart via electrodes disposed on the leads, e.g., typically near distal ends of the leads. In that case, the leads may position the electrodes with respect to various cardiac locations so that the pacemaker can deliver pulses to the appropriate locations. Leads may be used for sensing purposes, or for both sensing and stimulation purposes. Implantable leads are also used in neurological devices, muscular stimulation therapy, gastric system stimulators and devices that sense chemical conditions in a patient's blood.

Occasionally, patients that have implantable leads may benefit from a magnet resonance image being taken of a particular area of his or her body. Magnetic resonance imaging (MRI) techniques can achieve a very effective image of the soft tissues of the heart and vascular system. MRI procedures can also image these features without delivering ionizing radiation to the body of the patient, and, as a result, MRI procedures may be reliably and safely repeated. However, MRI devices may operate at frequencies of 10 megahertz or higher, which may cause energy to be transferred to the lead. In particular, the high frequency fields induce a voltage in the lead, causing the potential of the lead to be higher than the surrounding tissue. In effect, the lead behaves as an antenna. Current may flow from the electrode into the tissue proximate to the electrode due to induced voltage.

SUMMARY

This disclosure describes an electrode assembly and a lead including the electrode assembly. The electrode assembly includes at least two electrodes, such as a first electrode located near a distal end of the electrode assembly and a second electrode located near a proximal end of the electrode assembly. The electrode assembly also includes a conductive elongated coupler located between the first electrode and the second electrode. In one embodiment, the conductive elongated coupler is low frequency electrically coupled to the first electrode and capacitively coupled to the second electrode. At low frequencies and DC (e.g., during delivery of stimulation therapy), the capacitive coupling between the conductive elongated coupler and the second electrode is small and not a lot of current is redirected from the first electrode to the second electrode. However, at high frequencies (e.g., during an MRI scan or other procedure or environment having high frequency signals) the capacitive coupling between the conductive elongated coupler and the second electrode presents a low electrical impedance, resulting in a significant amount of induced current being redirected to the second electrode and dissipated into bodily fluid surrounding the second electrode. As such, the electrode assembly redirects current induced on the lead by high frequency signals away from the first electrode but does not significantly interfere with delivery of therapy (e.g., pacing pulses).

In one example, the disclosure is directed to an electrode assembly for a medical lead that includes a first electrode located near a distal end of the electrode assembly and an electrode shaft having a proximal end and a distal end. The distal end of the electrode shaft is configured to mechanically couple to the tip electrode and the proximal end of the electrode shaft is configured to mechanically couple to a first conductor of the electrical lead. The electrode assembly also includes a second electrode located near a proximal end of the electrode assembly and a conductive elongated coupler configured to electrically couple to one of the first electrode, the electrode shaft or the first conductor and capacitively couple to the second electrode such that at least a portion of current induced by a high frequency signal is redirected from the first electrode to the second electrode.

In another example, the disclosure is directed to a medical electrical lead comprising a lead body having a proximal end configured to couple to an implantable medical device and a distal end, a first conductor that extends from the proximal end of the lead body to the distal end of the lead body and an electrode assembly located at the distal end of the lead body. The electrode assembly includes a first electrode located near a distal end of the electrode assembly and an electrode shaft having a proximal end and a distal end. The distal end of the electrode shaft is configured to mechanically couple to the first electrode and the proximal end of the electrode shaft is configured to mechanically couple to the first conductor of the electrical lead. The electrode assembly also includes a second electrode located near a proximal end of the electrode assembly and a conductive elongated coupler configured to electrically couple to one of the first electrode, the electrode shaft or the first conductor and capacitively couple to the second electrode such that at least a portion of current induced by a high frequency signal is redirected from the first electrode to the second electrode.

This summary is intended to provide an overview of the subject matter described in this disclosure. It is not intended to provide an exclusive or exhaustive explanation of the techniques as described in detail within the accompanying drawings and description below. Further details of one or more examples are set forth in the accompanying drawings and the description below. Other features, objects, and advantages will be apparent from the description and drawings, and from the statements provided below.

DETAILED DESCRIPTION

The present disclosure provides an electrode assembly for a medical lead that redirects current induced by high frequency signals (e.g., high frequency RF signals greater than or equal to 1 MHz) away from an electrode, e.g., tip electrode, of the lead. Instead, the current induced by the high frequency signals is redirected via a conductive elongated coupler and dissipated via one or more other conductive structures, such as another electrode and/or a conductive sleeve head. By redirecting the current from the high frequency signals away from the tip electrode, the tip electrode does not experience high current density. This, in turn, reduces unintended heat generation in the tissue around the tip electrode. Consequently, a patient with a medical electrical lead may undergo medical procedures that utilize high frequency signals, such as an MRI procedure, without significantly affecting the operation of the medical electrical lead. The teachings of the present disclosure can be applied to low voltage leads, high voltage leads, retracted or non-retracted medical electrical leads. Low voltage leads typically operate at about 8 volts whereas high voltage leads can operate at about 800 volts.

Although described mainly in the context of MRI procedures, the techniques of this disclosure may also allow the patient to undergo other medical procedures that utilize high frequency signals that may affect operation of the medical electrical lead, such as an electrocautery procedure, diathermy procedure, ablation procedure, electrical therapy procedure, magnetic therapy procedure, or the like. Moreover, the electrode assemblies described in this disclosure may also reduce the effects of high frequency signals encountered in medical and non-medical environments, such in an environment with RFID reading devices including surgeries that utilize RFID tagged instruments, towels, or the like.

Figure 1:
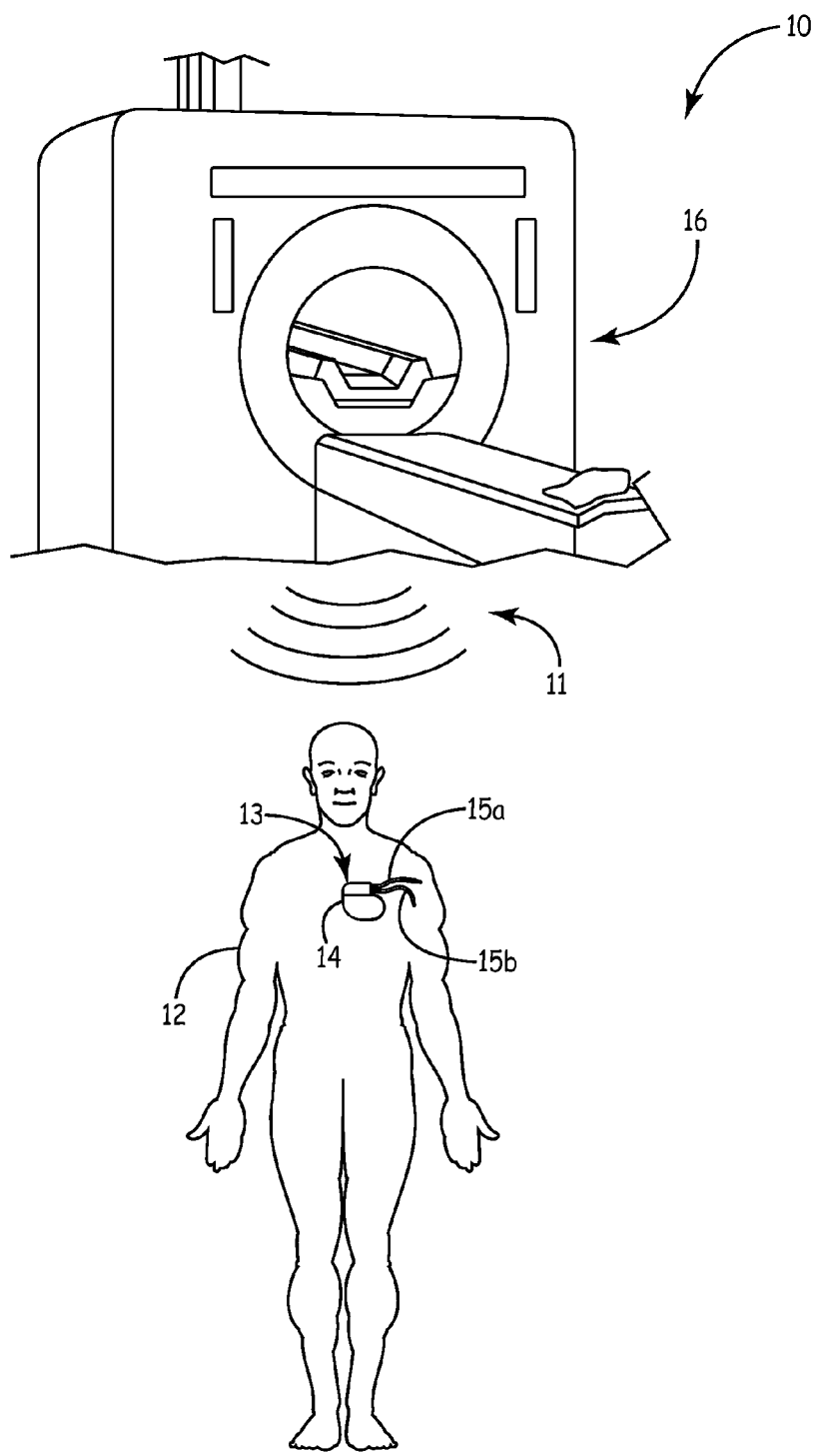
FIG. 1 is a conceptual diagram illustrating an environment in which an implantable medical system is exposed to a disruptive energy field.

FIG. 1 is a conceptual diagram illustrating an environment 10 in which an implantable medical system 13 is exposed to a disruptive energy field 11. Implantable medical system 13 includes an implantable medical device (IMD) 14 and one or more medical lead assemblies 15a,b that extend from the IMD 14 to a target location within patient 12. IMD 14 is implanted within patient 12 to provide therapy to and/or to monitor a physiological condition of patient 12. IMD 14 may be any of a variety of devices that provide therapy to patient 12, monitor a condition of patient 12, or both. For example, IMD 14 may be a device that provides electrical stimulation therapy via implantable lead assemblies 15a,b that include one or more electrodes. In some instances, IMD 14 may be a device that provides electrical stimulation therapy in the form of cardiac rhythm management therapy to a heart of patient 12 via leads implanted within one or more atria and/or ventricles of the heart. In other instances, IMD 14 may be a device that provides electrical stimulation to a tissue site of patient 12 proximate a muscle, organ or nerve, such as a tissue proximate a vagus nerve, spinal cord, brain, stomach, pelvic floor or the like.

Environment 10 includes an energy source that generates disruptive energy field 11 to which medical device system 13 is exposed. In the example illustrated in FIG. 1, the energy source or disruptive field source is an MRI scanner 16. Although the techniques of this disclosure are mainly described with respect to disruptive energy field 11 generated by MRI scanner 16, medical device system 13 may be used within environments in which other types of disruptive energy fields, medical and non-medical, are present. For example, medical device system 13 may be used in environments in which disruptive energy field 11 is generated by other sources, such as an external cardioversion device, external defibrillator, electrocautery device, diathermy device, ablation device, radiation therapy device, electrical therapy device, magnetic therapy device, RFID interrogation/reader device, or any other environment with devices that radiate energy to produce magnetic, electromagnetic, electric fields or other disruptive energy fields.

MRI scanner 16 uses magnetic and RF fields to produce images of body structures for diagnosing injuries, diseases and/or disorders. In particular, MRI scanner 16 may generate a static magnetic field, gradient magnetic fields and RF fields. The static magnetic field is a non time-varying magnetic field that is typically always present around MRI scanner 16 whether or not an MRI scan is in progress. Gradient magnetic fields are pulsed magnetic fields that are typically only present while the MRI scan is in progress. RF fields are pulsed high frequency RF fields that are also typically only present while the MRI scan is in progress. The magnitude, frequency or other characteristic of disruptive energy field 11 may vary based on the type of MRI scanner producing the field or the type of MRI scan being performed. A 1.5 T MRI scanner, for example, will produce a static magnetic field at about 1.5 Tesla and have a corresponding RF frequency of about 64 MHz. Without being bound by the theory, the strong magnetic fields in an MRI can induce aligned spins of sub-atomic particles and the high frequency RF pulses can be used to change the alignment or otherwise affect the sub-atomic particles within the patient 12.

Some or all of the various types of fields produced by MRI scanner 16 may interfere with operation of one or more components of medical device system 13, e.g., IMD 14 and/or medical lead assemblies 15a,b extending from IMD 14. In other words, one or more of the various types of fields produced by MRI scanner 16 may make up disruptive energy field 11. For example, the high frequency RF fields of MRI scanner 16 may induce current on one or more of medical lead assemblies 15a,b coupled to IMD 14. The induced current on lead assemblies 15a,b may result in high current density at an electrode-tissue interface, which, in turn, may cause unintended heat generation at the tissue around the electrode.

Such heating may compromise pacing and sensing thresholds at the site, which could result in reduced therapy efficacy.

As will be described in detail below, one or more implantable lead assemblies 15a,b extending from IMD 14 include an electrode assembly that redirects current caused by the high frequency signals of MRI scanner 16 (or other high frequency signals in the cases in which the source is not an MRI scanner) away from a tip electrode of the lead. Instead, the current caused by the high frequency signals are redirected via a conductive elongated coupler to another electrode of lead assemblies 15a,b and dissipated at the second electrode. In some embodiments, the current caused by the high frequency signals may be redirected and dissipated by a sleeve head or other conductive structure in addition to the other electrode. By redirecting the high frequency signals away from the tip electrode, the tip electrode does not experience high current density, which, in turn, reduces the amount of unintended heat generation at the tissue around the tip electrode.

IMD 14 may also be capable of operating in accordance with settings that are less susceptible to undesirable device operation during exposure to disruptive energy field 11, referred to herein as the "exposure mode" or "exposure operating mode." In the case of an exposure operating mode that specifically accounts for MRI scans, the mode may be referred to as an MR Conditional mode or an MR Safe mode. IMD 14 may be automatically or manually configured from a normal operating mode (e.g., the current operating mode) to the exposure operating mode prior to being exposed or upon being exposed to disruptive energy field 11 or environment 10.

When operating in the exposure operating mode, IMD 14 operates with different functionality compared to the normal operating mode. In some instances, IMD 14 may be configured to operate with reduced functionality. For example, IMD 14 may not provide sensing, not deliver therapy, deliver only a subset of possible therapies, not log collected data or the like. In other instances, IMD 14 may be operating with approximately the same functionality or even increased functionality in the exposure mode. For example, IMD 14 may use a different sensor or algorithm to detect cardiac activity of the heart of patient 12, such as pressure sensor measurements rather than electrical activity of the heart. Consequently, patient 12 with a medical electrical lead constructed in accordance with the techniques described herein may undergo an MRI procedure or other medical procedure without significantly affecting the operation of the medical electrical lead.

Figure 2:
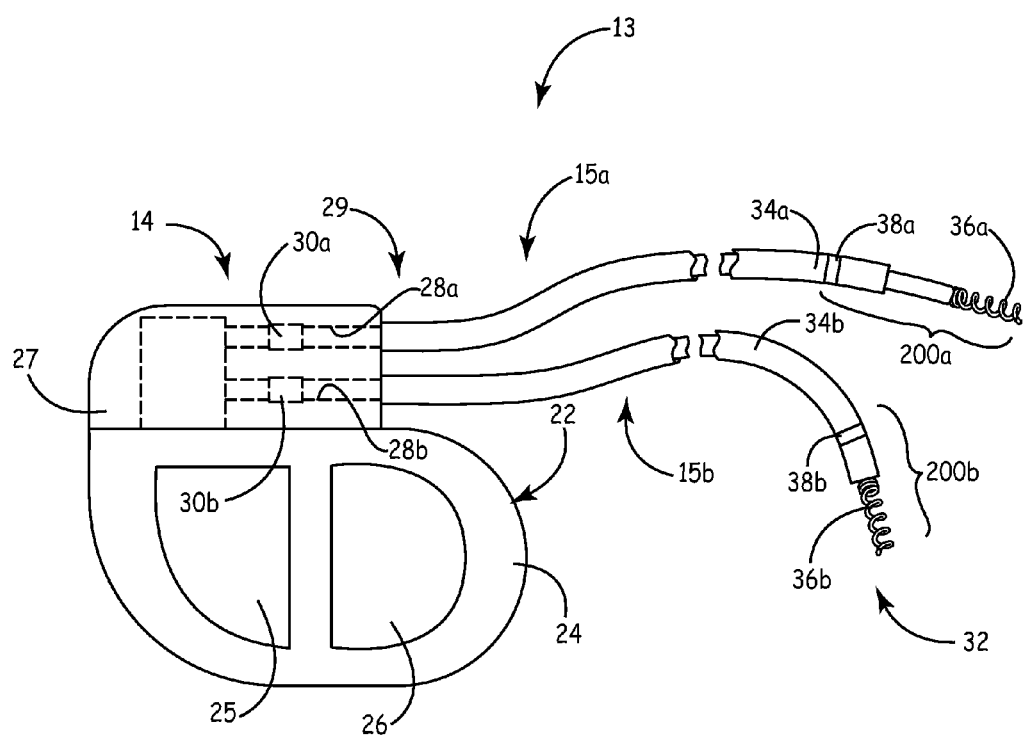
FIG. 2 is a conceptual diagram illustrating implantable medical system of FIG. 1.

FIG. 2 is a conceptual diagram illustrating implantable medical system 13 of FIG. 1. Medical system 13 includes IMD 14 and lead assemblies 15a, b. The IMD 14 may be an implantable cardiac device that senses electrical activity of a heart of patient 12 and/or provides electrical stimulation therapy to the heart of patient 12. The IMD 14 may, for example, be an implantable pacemaker, implantable cardioverter defibrillator (ICD), cardiac resynchronization therapy defibrillator (CRT-D), cardioverter device, or combinations thereof. The IMD 14 may alternatively be a non-cardiac implantable device, such as an implantable neurostimulator or other device that provides electrical stimulation therapy.

The IMD 14 can include an implantable case or body assembly 22 (sometimes referred to as a housing). The implantable case 22 can be formed of appropriate materials and include appropriate features, such as a hermetically sealed body wall 24. The body wall 24 can be made of a substantially inert material or of a conducting material. Contained within or associated with the case 22 can be a power device 25 (e.g., battery) and a controller assembly 26. The controller assembly 26 can include a circuit board having one or more electrical components, such as one or more processors, memories, transmitters, receivers, and other appropriation components.

The IMD 14 also includes a connector body 27 that extends from or is integrated with the case 22. The connector body 27 can include one or more ports 28a,b that interconnect with one or more connector terminals 30a,b located on a proximal end 29 of lead assemblies 15a,b. The lead assemblies 15a,b generally include respective lead bodies 34a,b each having a respective electrode assembly 200a,b located at a distal end 32 of lead assemblies 15a,b. In the example illustrated in FIG. 2, electrode assembly 200a,b each include a respective ring electrode 38a,b and tip electrode 36a,b. As will be described in further detail herein, electrode assemblies 200a,b each include a conductive elongated coupler (not shown in FIG. 2) located between ring electrodes 38a,b and tip electrodes 36a,b of respective electrode assemblies 200a,b. Current induced by high frequency signals is redirected from tip electrodes 36a,b to respective ring electrodes 38a,b (or others not shown) via the conductive elongated coupler.

A fixation mechanism can also be included with the lead assemblies 15a,b to affix the tip electrodes 36a,b relative to or in a selected tissue, muscle, nerve or other location within the patient 12. The fixation mechanism can be near the tip electrodes 36a,b or define a portion of the tip electrodes 36a,b. In the example illustrated in FIG. 2, tip electrodes 36a,b are formed to define the fixation mechanism. Tip electrodes 36a,b take the form of extendable helically shaped electrodes to facilitate fixation of the distal end of electrode assemblies 200a,b to patient 12. In other instances, the fixation mechanism may be a separate structure from tip electrode 36a,b. Fixation mechanisms can be any appropriate type, including a grapple mechanism, a helical or screw mechanism, a drug-coated connection mechanism in which the drug(s) serves to reduce infection and/or swelling of the tissue, or other attachment mechanism. In addition, the lead assemblies 15a,b can define an active or passive lead assembly, as discussed herein. Moreover, both of the electrical lead assemblies 15a,b may be a single lead assembly type or mixed in any appropriate manner.

The various conductors and electrical components of lead bodies 34a,b can be encased in silicone, polyurethane, fluoropolymers, mixtures thereof, and other appropriate materials. For example, at least one or more conductors (not shown in FIG. 2) can extend within lead bodies 34a,b from the connector 30a,b to engage the ring electrode 38a,b and tip electrode 36a,b, respectively. In other words, each of tip electrodes 36a,b and ring electrodes 38a,b is electrically coupled to a respective conductor within its associated lead bodies 34a,b. For example, a first electrical conductor can extend along the length of lead body 34a from connector body 27 and electrically couple to tip electrode 36a and a second electrical conductor can extend along the length of lead body 34a from connector body 27 and electrically couple to ring electrode 38a. The respective conductors may couple to circuitry, such as a therapy module or a sensing module, of IMD 14 via connections in connector body 27. The electrical conductors transmit therapy from the therapy module within IMD 14 to one or both of the electrodes and transmit sensed electrical signals from the electrodes to the sensing module within IMD 14. The conductors can be one piece or multiple components that are interconnected. The conductor can also be cannulated or include a solid or non-cannulated cable. Additionally, the conductors may include one or more filers.

When IMD 14 is capable of delivering electrical stimulation therapy, IMD 14 delivers the therapy (e.g., pacing pulses) to patient 12 via any combination of electrodes to cause depolarization of cardiac tissue of the heart of patient 12. For example, IMD 14 may deliver bipolar pacing pulses to patient 12 via electrodes 36a and 38a and/or electrodes 36b and 38b. In another example, IMD 14 may deliver unipolar pacing pulses to patient 12 using a housing electrode (not shown) in conjunction with one of electrodes 36a and/or 36b. The housing electrode may be formed integrally with an outer surface of the case 22 of IMD 14 or otherwise coupled to the housing. In some examples, the housing electrode is defined by an uninsulated portion of an outward facing portion of case 22. IMD 14 can include various features or mechanisms to defibrillate or pace the heart, including a processor associated with the electronics component 26 within the case 22. The processor can be programmed to control driving a current through the lead bodies 34a,b to the tip electrodes 36a,b to defibrillate or pace the heart.

Electrodes 36a,b and/or 38a,b may also sense electrical signals attendant to the depolarization and repolarization of the heart of patient 12 and the sensed electrical signals are conducted to IMD 14 via one or more conductors of respective lead assemblies 15a,b. IMD 14 may use any combinations of the electrodes and/or the housing electrode for unipolar or bipolar sensing. As such, the configurations of electrodes used by IMD 14 for sensing and pacing may be unipolar or bipolar depending on the application. IMD 14 may analyze the sensed signals to monitor a rhythm of the heart of patient 12 to detect an arrhythmia of the heart, e.g., tachycardia, bradycardia, fibrillation or the like. In some instances, IMD 14 provides pacing pulses (or other therapy) to the heart based on the cardiac signals sensed within the heart. In other words, pacing may be responsive to the sensed events.

Figure 3:
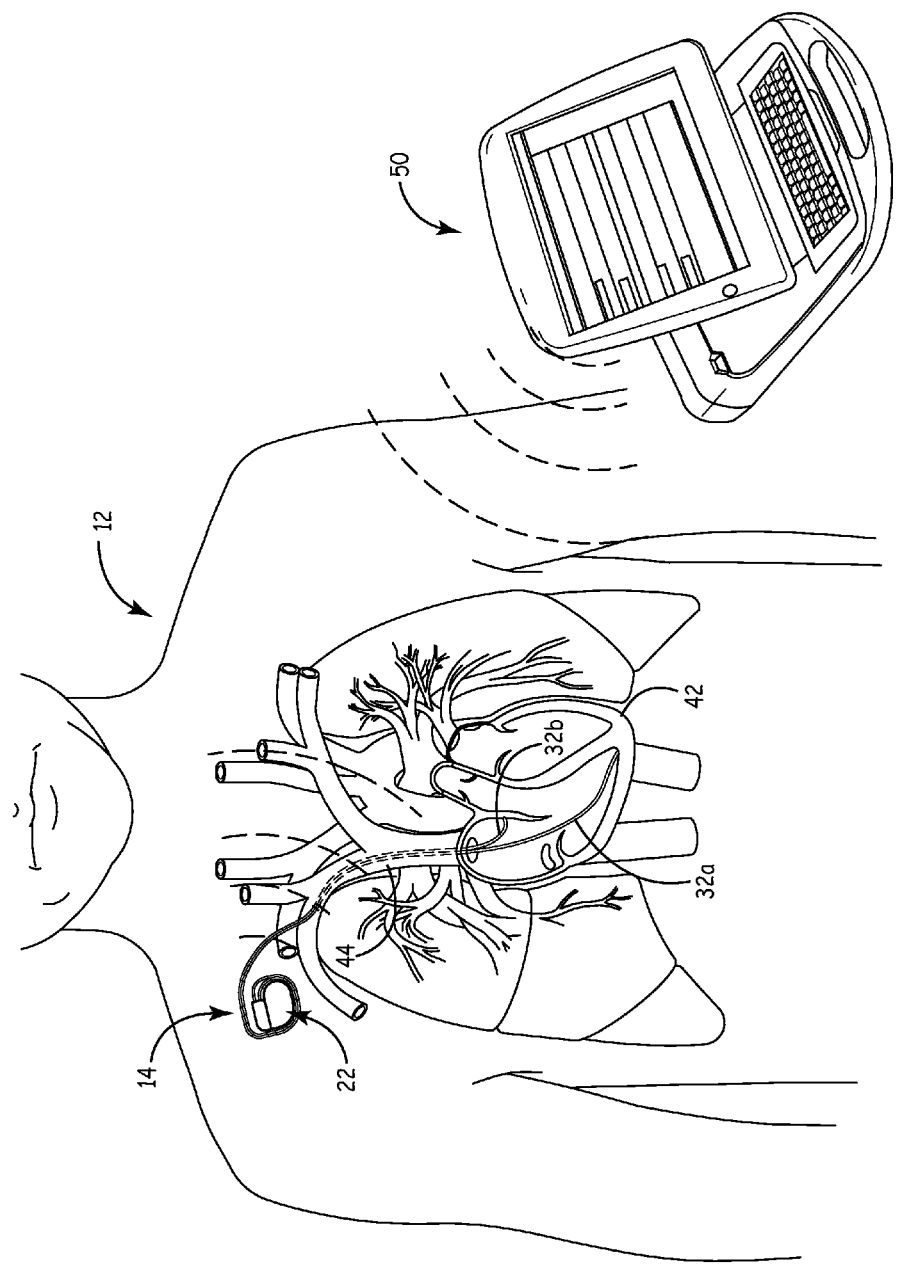
FIG. 3 is a conceptual diagram that illustrates implantable medical system implanted in a patient in conjunction with a programming device.

FIG. 3 is a conceptual diagram that illustrates implantable medical system 13 in conjunction with a programming device 50. Implantable medical system 13, including the IMD 14 and lead assemblies 15a,b are illustrated as being implanted within a heart 42 of patient 12. IMD 14 and lead assemblies 15a,b can be implanted using substantially known procedures. For example, an incision can be made in a chest wall or an abdomen wall of the patient 12 and the leads 15a,b can be passed through selected veins to selected portions of a heart 42 of the patient 12. The device body 22 can also be positioned through the incision into a chest wall or abdominal wall of the patient 12. In a selected procedure, the leads 15a,b can be passed through a superior vena cava 44 of the patient 12. The tip electrodes 36a,b can be positioned at various positions in the heart 42, such as at the ventricles or atriums thereof. In the example of FIG. 3, lead 15a is located within a right ventricle of heart 42 and lead 15b is located within a right atrium of heart 42. The position of the leads 15a,b and/or the electrodes of leads 15a,b can be selected for pacing, defibrillation, sensing, cardiac resynchronization, cardioversion or other appropriate therapy/sensing functionality. The specific implantation procedure, position of the electrodes, and the like can depend upon the patient 12, the surgeon performing the procedure, the specifics of the lead assemblies 15a,b, the desired treatment, or other considerations.

IMD 14 may wirelessly communicate with programming device 50. The programming device 50 can include a telemetry module that is operable to wirelessly transmit and/or receive a signal to or from a telemetry module or processor within the case body 22 of IMD 14. A user, such as a physician, technician, or other clinician, may interact with programming device 50 to communicate with IMD 14.

The user may also interact with programming device 50 to program IMD 14, e.g., select values for operational parameters of IMD 14. For electrical stimulation therapies, for example, the user may interact with programming device 50 to program a therapy progression, select an electrode or combination of electrodes of leads of IMD 14 to use for delivering electrical stimulation (pulses or shocks), select parameters for the electrical pulse or shock (e.g., pulse amplitude, pulse width, or pulse rate), select electrodes or sensors for use in detecting a physiological parameter of patient 12, or the like. By programming these parameters, the physician or other user can attempt to generate an efficacious therapy for patient 12 that is delivered via the selected electrodes. The operating parameters may be parameters of a normal operating mode or an exposure operating mode.

The user may interact with programming device 50 to manually configure IMD 14 into and/or out of the exposure operating mode. The user may, for example, interact with programming device 50 to program IMD 14 into the exposure operating mode prior to patient 12 undergoing a medical procedure in which IMD 14 will be exposed to a disruptive energy field 11, e.g., before undergoing a MRI scan. The user may also reprogram IMD 14 from the exposure mode to a normal mode after the MRI scan is finished.

The user may further interact with programming device 50 to retrieve physiological information, diagnostic information, logs of delivered therapies, or an assessment of the performance or integrity of IMD 14, such as leads or a power source of IMD 14. For example, the user may use programming device 50 to retrieve information from IMD 14 regarding sensed physiological parameters of patient 12, such as electrical depolarization/repolarization signals from the heart (referred to as an "electrogram" or EGM), intracardiac or intravascular pressure, activity, posture, respiration or thoracic impedance.

Programming device 50 may communicate with IMD 14 via wireless communication using any techniques known in the art. Examples of communication techniques may include, for example, magnetic telemetry, low frequency telemetry, RF telemetry, tissue conductance telemetry (in which the body is used as a conductor), or acoustic telemetry, but other techniques are also contemplated. In some instances, programming device 50 and IMD 14 may communicate in the 402-405 MHz frequency band in accordance with the Medical Implant Communications Service (MICS) frequency band regulation, in the 401-402 MHz or 405-406 MHz frequency bands in accordance with the Medical External Data Service (MEDS) band regulations, in the unlicensed industrial, scientific and medical (ISM) band, or other frequency band.

Programming device 50 may be a dedicated hardware device with dedicated software for programming of IMD 14. Alternatively, programming device 50 may be an off-the-shelf computing device running an application that enables programming device 50 to program IMD 14. In some examples, programming device 50 may be a handheld computing device or a computer workstation. Programming device 50 may, in some instances, include a programming head that may be placed proximate to the patient's body near the implant site of IMD 14 in order to improve the quality or security of communication between IMD 14 and programming device 50. Programming device 50 may include one or more processors, such as one or more microprocessors, digital signal processors (DSPs), application specific integrated circuits (ASICs), field-programmable gate arrays (FPGAs), programmable logic circuitry, or the like, that may perform various functions and operations, such as those described herein.

The configuration of implantable medical system 13 illustrated in FIGS. 2 and 3 is merely an example. In other examples, implantable medical system 13 may include more or fewer leads extending from IMD 14. For example, IMD 14 may be coupled to three leads, e.g., a third lead implanted within a left ventricle of the heart 42. In another example, IMD 14 may be coupled to a single lead that is implanted within either an atrium or ventricle of the heart 42. As such, IMD 14 may be used for single chamber or multi-chamber cardiac rhythm management therapy.

In addition to more or fewer leads, each of the leads may include more or fewer electrodes. In instances in which IMD 14 is used for therapy other than pacing, e.g., defibrillation or cardioversion, the leads may include elongated electrodes, which may, in some instances, take the form of a coil. IMD 14 may deliver defibrillation or cardioversion shocks to the heart via any combination of the elongated electrodes and housing electrode. As another example, medical system 13 may include leads with a plurality of ring electrodes, e.g., as used in some implantable neurostimulators.

Figure 4A:
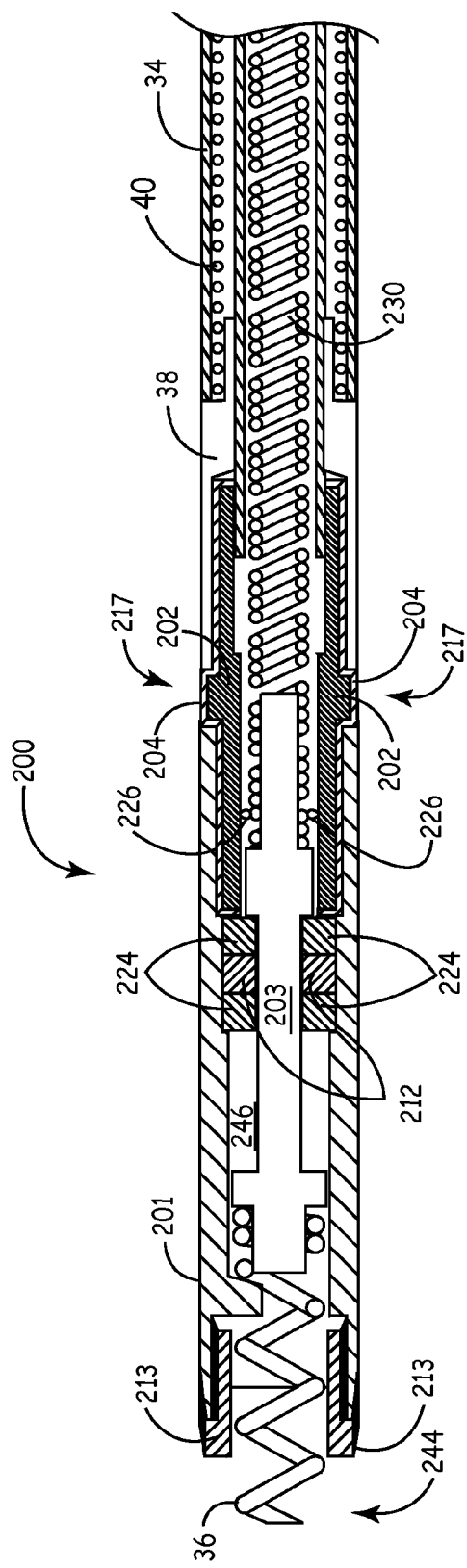
FIGS. 4A-4C are schematic diagrams illustrating an example electrode assembly in further detail.
Figure 4B:
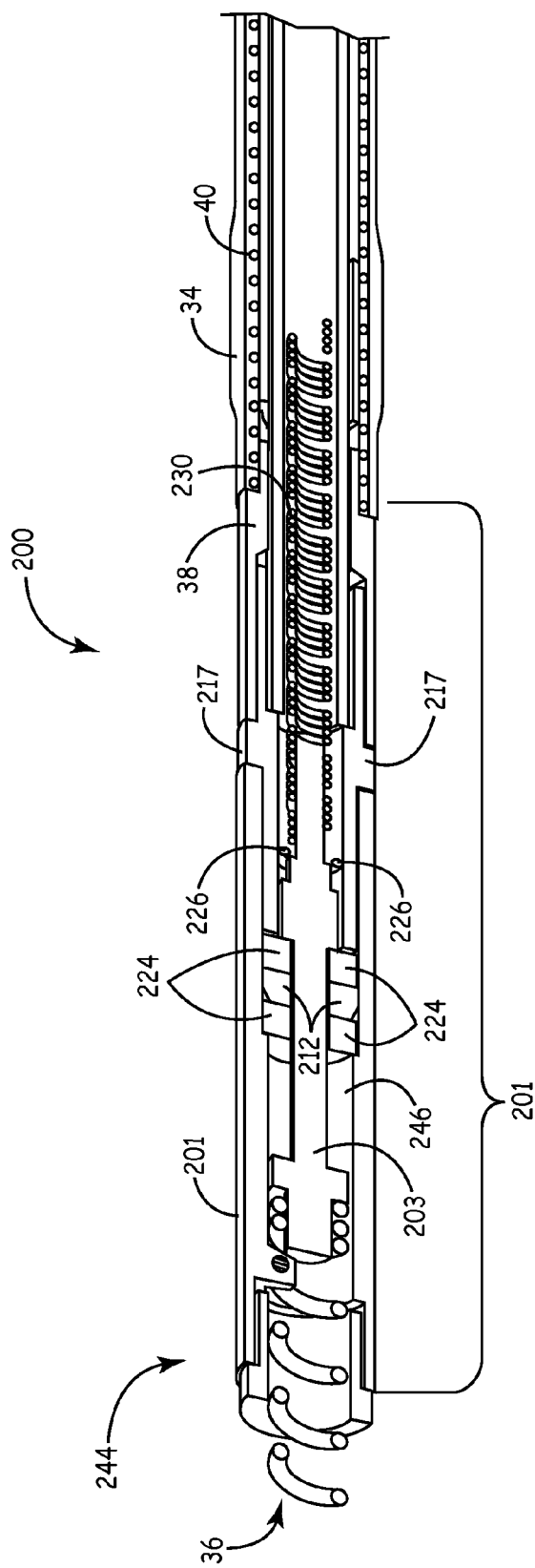
Figure 4C:
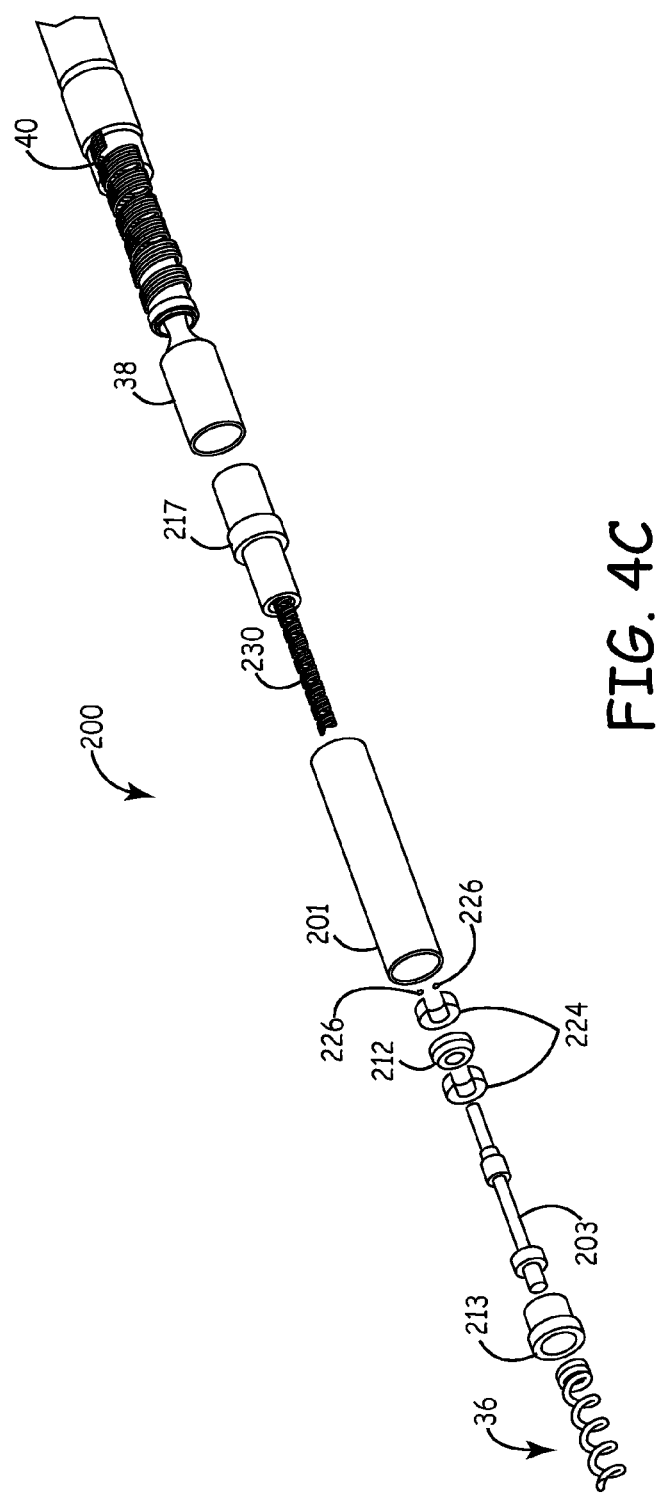

FIGS. 4A-4C are schematic diagrams illustrating example electrode assembly 200 in further detail. Electrode assembly 200 may correspond with electrode assembly 200a of lead assembly 15a or electrode assembly 200b of lead assembly 15b of FIG. 2. Electrode assembly 200 includes a tip electrode 36 and a ring electrode 38. However, electrode assembly 200 may include more than two electrodes.

Electrode assembly 200 includes a tip conductor 230 that extends along a length of the lead and electrically couples to a conductive electrode shaft 203. Tip conductor 230 and electrode shaft 203 may be mechanically coupled in addition to being electrically coupled. Tip electrode 36 is electrically and, in some instances, mechanically coupled to the opposite end of electrode shaft 203. The mechanical coupling may be achieved via spot welding, clinching or other suitable mechanism. Conductive electrode shaft 203 and/or tip electrode 36 may be made from any conductive material, including titanium, titanium alloy, conductive polymers, and/or other suitably conductive material. Tip conductor 230 may, in some instances, be separate pieces or multiple components that are interconnected (e.g., a multifilar wire). The electrical conductors can also be cannulated or include a solid or non-cannulated cable.

Tip electrode 36 may be retractable such that it may be controlled to extend from and retract within the distal end of electrode assembly 200. During implantation, a user may interact with lead assembly 15 to rotate tip conductor 230, which causes electrode shaft 203 to rotate and extend tip electrode 36 from the distal end of electrode assembly 200. In this manner, tip electrode may be screwed into the target tissue location within patient 12. As such, tip conductor 230 may have sufficient rigidity to assist in attaching electrode assembly 200 to the target tissue location while being flexible to navigate through a body lumen of patient 12, e.g., through one or more veins. In other instances, electrode shaft 203 may be formed to receive a stylet to allow a user to rotate electrode shaft 203 to extend and/or retract tip electrode 36.

Lead assembly 15 also includes a ring conductor 40 located within lead body 34 and extending along a length of lead 15 to electrically couple to ring electrode 38. Ring conductor 40 may be comprised of one or more conductive wires each surrounded by a respective insulative jacket. A proximal end of ring electrode 38 may be formed to receive a portion of ring conductor 40. Ring conductor 40 and ring electrode 38 may be mechanically coupled (e.g., via spot welding, clinching or other mechanism) in addition to being electrically coupled. Ring electrode 38 may have a cylindrical shape, but other shaped electrodes may be utilized in place of a ring electrode. Ring conductor 40 is illustrated in FIGS. 4A-4C as having a larger diameter than tip conductor 230. In other instances, tip conductor 230 may have a larger diameter than ring conductor 40 or may have an equal diameter and run the length of the lead body 34 intertwined with one another.

At the proximal end 29 of lead 15, tip conductor 230 and ring conductor 40 are electrically coupled to one or more electrical components of controller assembly 26, such as an electrical stimulation module or sensing module. Electrical stimulation may be delivered from IMD 14 to tip electrode 36 and/or ring electrode 38 and sensed electrical signals may be delivered from tip electrode 36 and/or ring electrode 38 via their respective conductors.

Lead assembly 15 can be formed to counteract or interact with various environmental factors. For example, the lead assembly 15 can include features or portions to redirect and/or dissipate a portion of thermal energy created by an induced current. As described above, the induced currents can be created due to high frequency signals acting on the conductors of the lead assembly 15.

As described above, the patient 12 which has the implanted medical system 13 may receive a certain therapy or diagnostic technique, such as an MRI scan that exposes lead assembly 15 to high frequency RF pulses and strong magnetic fields to create image data regarding the patient 12. The strong magnetic fields and RF pulses can induce currents within the lead assemblies 15a,b of the IMD 14. The current induced in the lead assemblies 15a,b can cause certain effects, including heating, of the various lead components and/or tissue near the lead. According to various embodiments, such as those discussed herein, components or mechanisms can be provided to reduce or eliminate the amount of current at the tip electrode 36 or increase an area over which the current or thermal energy can be dissipated.

Figure 5:
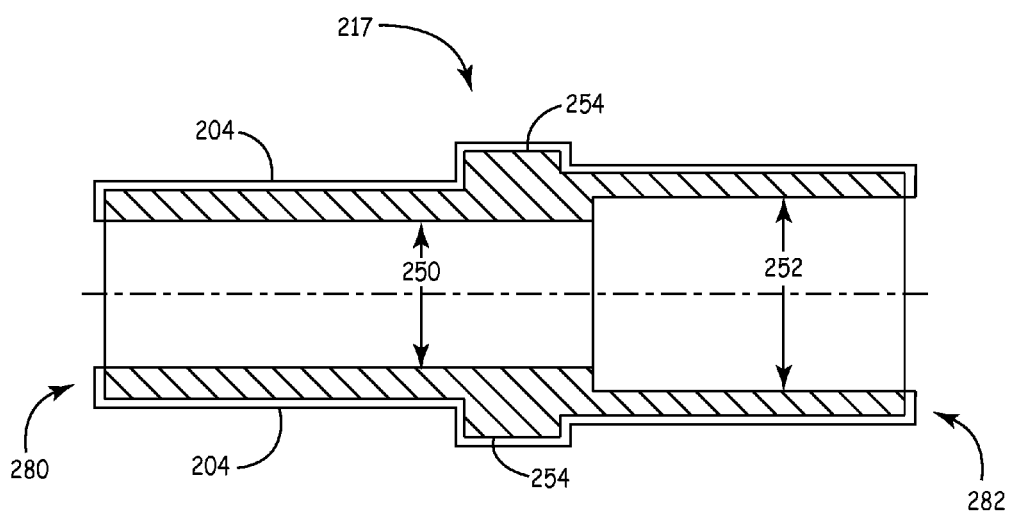
FIG. 5 is a cross-sectional view of an example conductive coupler.

As schematically illustrated in FIGS. 4A-4C, the electrode assembly 200 is located at the distal end 32 of the lead assembly 15. The electrode assembly 200 includes a conductive elongated coupler 217 located between tip electrode 36 and ring electrode 38. Coupler 217 may house a portion of conductive electrode shaft 203 and tip conductor 230 coupled thereto. The coupler 217 is depicted as substantially cylindrical. However, other suitable shapes can be used. Coupler 217 can include one or more mating elements in order to securely mate with sleeve head 201, ring electrode 38 and a torque coil 230 and/or electrode shaft 203 to provide rigidity to the lead for implantation purposes. For example, as depicted in FIG. 5, coupler 217 can include a stepped inner diameter such that a first inner diameter 250 is configured to receive electrode shaft 203 and a second inner diameter 252 is configured to receive tip conductor 230 around the shaft 203. Coupler 217 can also include an outer protrusion such as an outer ring 254 or shelf to enable coupler 217 to be securely mated between sleeve head 201 and ring electrode 38.

In the example illustrated in FIGS. 4A-4C, conductive coupler 217 is electrically coupled to tip conductor 230 via a spring clip 226. In other words, spring clip 226 serves to connect tip conductor 230 to coupler 217. However, conductive coupler 217 may be electrically coupled to tip conductor 230 via a different connection mechanism other than spring clip 226. The connection mechanism may be any conductive member that physically contacts a conductive portion of tip conductor 230. Alternatively, conductive coupler 217 may be electrically connected to electrode shaft 203 instead of tip conductor 230 or be electrically coupled to both tip conductor 230 and electrode shaft 203. For example, conductive coupler 217 may be configured such that when assembled conductive coupler 217 may be in direct contact with electrode shaft 203 or tip conductor 230. At least a portion of the current induced on tip conductor 230 by high frequency signals is redirected away from tip electrode 36.

Coupler 217 may, in one example, be formed of an electrically conductive material 202 and an insulative layer 204 wrapped or introduced around at least a portion of the outer diameter of the outer surface of conductive material 202. Insulating material 204 can cover or surround all or at least part of the outer surface of conductive element 202 of coupler 217. In instances in which the insulating material 204 only covers or surrounds a portion of the outer surface of conductive element 202, insulating material 204 covers at least the portion of conductive element 202 located adjacent to ring electrode 38 and/or covers portions of the conductive element 202 that are exposed to bodily fluids (e.g., the portion of coupler 217 located between the ring electrode 38 and sleeve head 201). In this manner, insulating material 204 separates the conductive element 202 from the conductive ring electrode 38 such that there is no direct electrical connection between coupler 217 and ring electrode 38. Instead, coupler 217 and ring electrode 38 are capacitively coupled (or other non-conductive coupling) as will be described in further detail below.

In the case of capacitive coupling, conductive coupler 217 and ring electrode 38 may be viewed as a capacitor with ring electrode 38 being a first capacitive plate, a portion of conductive coupler 217 as a second capacitive plate, and the insulating material 204 being the dielectric between the two plates. At low frequencies and DC (e.g., during delivery of stimulation therapy), the capacitive coupling between conductive coupler 217 and ring electrode 38 presents a high impedance allowing little current to be redirected to ring electrode 38. However, at high frequencies (e.g., during an MRI scan) the capacitive coupling between conductive coupler 217 and ring electrode 38 presents a low impedance, resulting in a significant amount of the induced current or energy being redirected to ring electrode 38. As such, electrode assembly 200 redirects current from high frequency signals away from tip electrode 36 but does not significantly interfere with delivery of therapy (e.g., pacing pulses).

In one or more embodiments, conductive element 202 of coupler 217 may be cylindrically shaped (e.g. ring, etc.). However, conductive element 202 of coupler 217 may take on any a variety of other shapes. Conductive element 202 may comprise materials that are chemically stable, biocompatible, and x-ray transparent. Exemplary material used to form conductive element 202 includes titanium, titanium alloy, conductive polymers, and/or other suitable materials.

Figure 6:
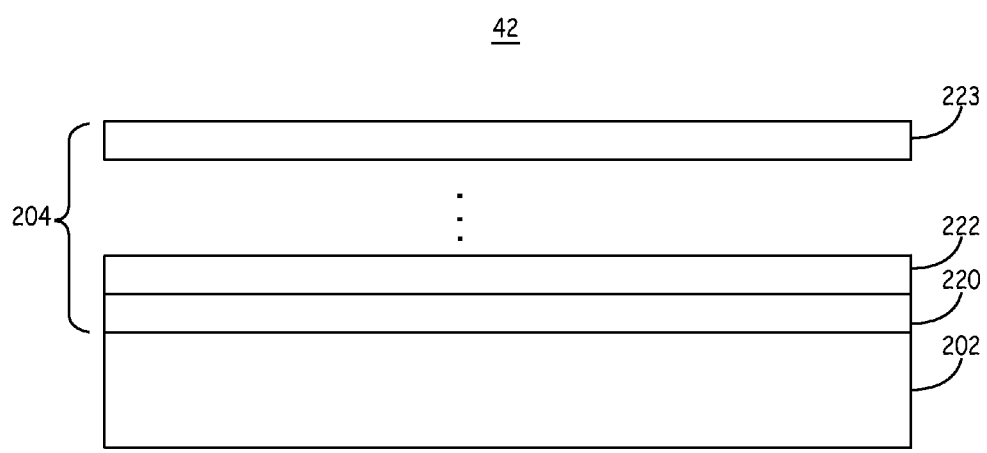
FIG. 6 depicts multiple layers of insulating material over a conductive element of a component of an electrode assembly.

Referring to FIG. 6, insulative material 204 is formed over at least a portion of conductive element 202. Insulating material 204 will affect the capacitance of conductive coupler 217 and reduce the effect of conductive coupler 217 on the tip to tissue interface impedance. For example, as the thickness of insulating material 204 increases, the capacitance associated with conductive coupler 217 decreases and the impedance of conductive coupler 217 to second (alternative electrode) increases. As a result the amount of induced current redirected through conductive couple 217 is reduced, but there is less interference with therapy signals delivered by IMD 14. As the thickness of insulating material 204 decreases, the capacitance associated with conductive coupler 217 increases and the impedance of conductive coupler 217 to second (alternative electrode) decreases. As a result the amount of induced current redirected through conductive coupler 217 is increased, but there is more interference with therapy delivered by IMD 14. As such, the thickness of insulating material 204 may be adjusted by a therapy system designer to achieve a satisfactory tradeoff between low frequency and high frequency performance.

Insulative material 204 may be formed from a single layer or multiple layers such as first layer 220, second layer 222, and Nth layer 223. Each layer may comprise different insulating materials, two or more different insulating materials, or the same insulating materials. A thickness of insulative material 204 depends on the dielectric associated with insulative material 204 and an area of sleeve head 201. For an insulative material 204 having a dielectric constant of 4 and an area of 22 $mm^2$ a desired thickness may be less than 4 mils (100 micrometers). Insulative material 204 may be formed from any of a wide variety of insulating materials. Exemplary insulating material includes at least one or more of Parylene, polyamide, metal oxides, polyimide, urethane, silicone, tetrafluroethylene (ETFE), polytetrafluroethylene (PTFE), ceramics, or the like. Numerous techniques may be employed to introduce insulating material 204 over the outside of coupler 217 and/or partially inside coupler 217. Exemplary techniques include chemical vapor deposition, dip coating, or thermal extrusion.

Electrode assembly 200 also includes a sleeve head 201 that houses all, or at least a portion, of tip electrode 36 (depending on whether tip electrode is refracted or not), all or a portion of conductive electrode shaft 203, sealer 212, rings 224 and coupler 217. Sleeve head 201 may be of a generally cylindrical (e.g., ring) shape. In the embodiment depicted in FIGS. 4A-4C, sleeve head 201 comprises an insulative material and is not electrically conductive. Exemplary material used to form sleeve head 201 can comprise the same material as insulative material 204 or different material. In one or more embodiments, sleeve head 201 can comprise other polymeric materials.

Sleeve head 201 may be in contact with and, in some instances, mechanically connected to coupler 217. Additionally, sleeve head 201 may be in contact with and, in some instances, mechanically coupled to, a sealer 212 (also referred to as a sealing washer). Sealer 212 is also in contact with electrode shaft 203. Sealer 212 prevents fluid from passing through space 246 into the lumen defined by the lead body and housing tip conductor 230, ring conductor 40 and the like. Referring to FIGS. 13A-13D, sealer 212 is substantially ring (e.g. o-ring) or disk shaped but other suitable shapes may also be employed. In one embodiment, sealer 212 is defined by X1, X2 and radius (r1). X1 ranges from about 0.1 mm to about 0.50 mm, X2 extends from about 0.1 mm to about 1.0 mm, and r1 extends from about 0.5 mm to about 1.0 mm. Curved end 252 extends to about 1.25 mm from the center of shaft 203 and includes a curve defined by a radius of about 0.5 mm. These dimensions are provided for exemplary purposes only and should not be considered limiting. The dimensions of sealer 212 will depend on the size and/or configuration of other components of lead assembly 15. Sealer 212 may be formed from a non-conductive or conductive material or both.

Electrode assembly 200 may also include one more rings, such as parallel rings 224 (e.g., C-rings) illustrated in FIGS. 4A-4A and 13A-13D, that may hold sealer 212 in place and/or act as markers. In some instances, sleeve head 201 and/or electrode shaft 203 may also be in contact with one or more rings. Rings 224 of FIGS. 4A-C and 13A-13D are shaped as a C-ring to receive sealer 212. However, rings of other shapes may be used. Rings 224 have an outer diameter of about 1.5 mm, an inner diameter of about 0.7 mm, and a thickness that ranges from about 0.25 mm (T1) to about 0.5 mm (T2). Rings 224 may be comprised of a non-conductive material or of a conductive material or both.

Electrode assembly 200 may also include a monolithic control release device (MCRD) 213 that protrudes from an inner diameter of a sleeve head 201. MCRD 213 can provide chronic steroid elution to maintain a low pacing threshold for implantable medical system 13. Other portions can also be associated with the lead assemblies 15.

Electrode assembly 200 of FIGS. 4A-4C is one example of an electrode assembly in accordance with this disclosure. Modifications may be made while still remaining within the scope of this disclosure.

Figure 7:
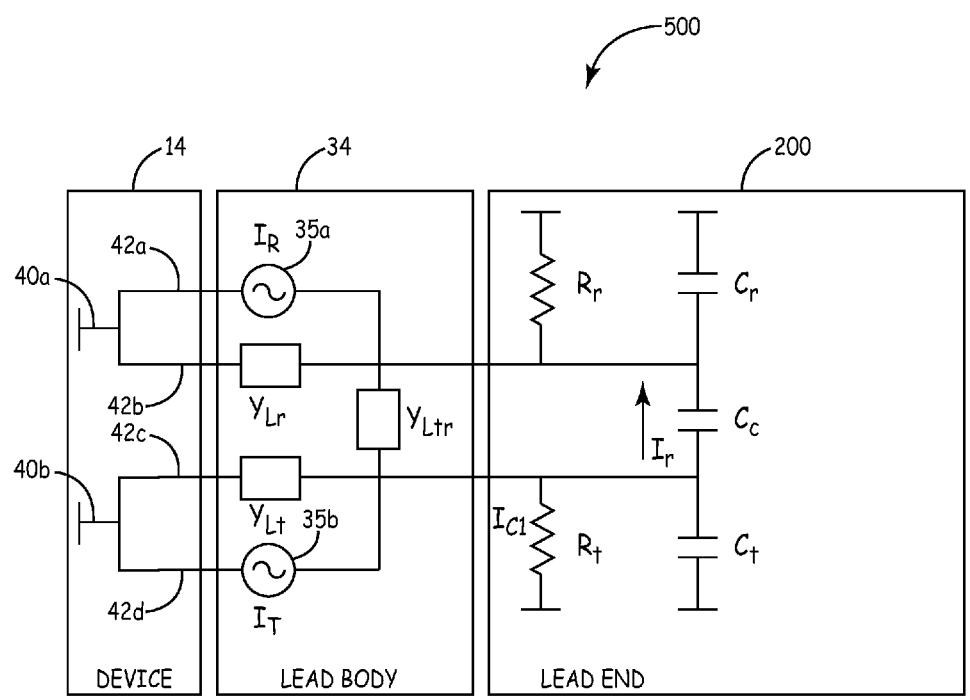
FIG. 7 depicts a circuit diagram illustrating an example circuit representing medical system.

FIG. 7 depicts a circuit diagram 500 illustrating an example circuit representing medical system 13. Circuit diagram 500 represents each of the IMD 14, the lead body 34, and electrode assembly 200 as one or more electrical components. First and second electrically conductive lines, wires or traces 40a,b extend from the connector body 27 of IMD 14 to the lead body 34 through conductive paths 42a-d. Although not illustrated in FIG. 7, IMD 14 may include some resistance and capacitance associated with feed through capacitors, wires or traces 40a,b, or the like, and may include a voltage source representing a stimulation generator.

Current sources 35a ($I_R$), 35b ($I_T$) are used to represent or model current induced in elongated conductors that extend along the lead body 34 from connector body 27 to the tip electrode 36 and the ring electrode 38 (e.g., tip conductor 230 and ring conductor 40, respectively). To simplify the discussion of the circuit 500, an admittance network is used to merely provide a high level representation of complexities that are associated with lead body 34. For example, lead body 34 is represented as having a lead ring admittance $Y_{Lr}$, a tip-to-ring admittance $Y_{Ltr}$, and a lead tip admittance $Y_{Lt}$. While the tip conductor 230 for tip electrode 36 is not directly electrically or mechanically connected to the ring conductor 40 for the ring electrode 38, $Y_{Ltr}$ exists between the ring conductor and tip conductor due solely, or, at least in part, to inductive and/or capacitive coupling that occurs between the tip conductor 230 and the ring conductor 40.

The electrode assembly 200 includes a coupler capacitance $C_c$, representing conductive coupler 217, that is used to redirect a portion of the induced current $I_T$ away from tip electrode 36. The electrode assembly 200 also includes resistors and capacitors that represent the tissue interface impedances, including a tip-to-tissue resistance $R_t$, a ring-to-tissue resistance $R_r$, a tip-to-tissue capacitance $C_t$, and a ring-to-tissue capacitance $C_r$. Although not electrically or mechanically connected to one another, an impedance may also exist between the tip electrode 36 and the ring electrode 38 due solely, or, at least in part, to inductive and/or capacitive coupling that occurs between the tip electrode 36 and the ring electrode 38. Because this impedance has only a very negligible effect on the electrical characteristics of electrode assembly 200, these impedances are not illustrated in circuit 500.

Exemplary values for the electrical components representing the electrode assembly 200 include $C_t$ is approximately 1 micro Farad (µF), $R_t$ is approximately 500 Ohm (Ω), $C_r$ at approximately 10 µF, $R_r$ is approximately 100Ω and $C_c$ is greater than approximately 250 pF. In one example $C_c$ may be between approximately 250 pF and 1 nF. For a sleeve head having a surface area of approximately 22 square millimeters (mm²) and an insulating material 204 having a dielectric constant of approximately 4, for instance, a insulating layer thickness of approximately 68 micrometers provides an impedance of approximately 10 Ohms and a capacitance of approximately 250 pF, a thickness of approximately 34 micrometers provides an impedance of approximately 5 Ohms and a capacitance of approximately 500 pF, and a thickness of approximately 17 micrometers provides an impedance of approximately 2.5 Ohms and a capacitance of approximately 1 nF. These values are only exemplary in nature. The components of circuit 500 representing the electrical characteristics of electrode assembly 200 may be take on different values depending on the construction of electrode assembly 200, e.g., based on the surface area of tip electrode 36, the surface area of ring electrode 38, the size of coupler 217, the thickness of insulative layer 204 of coupler 217, the material from which electrodes 36, 38 or coupler 217 are constructed of and the like.

If a patient is exposed to an MRI, current $I_T$ represents the current induced on tip conductor 230 by the high frequency signal. A large portion of the induced current $I_T$ would be dissipated via the tip electrode 36 in a conventional lead design. However, a lead constructed in accordance with the techniques of this disclosure redirects at least a portion of the induced current $I_T$ to the coupler 217 and then to the ring electrode 38, where it is dissipated to tissue or bodily fluid in contact with ring electrode 38. Since the frequency of disruptive energy field 11 is large, the impedance associated with $C_c$ is small resulting in a large portion of the total current flowing through $C_c$ representing conductive coupler 217 to $C_r$ and $R_r$ representing ring electrode 38. The current that passes through conductive coupler 217 to ring electrode 38 is represented as $I_r$. The remainder of the induced current passes through resistor $R_t$ and capacitor $C_t$ representing tip electrode 36.

In one example, $I_r$ may be greater than or equal to approximately 80% of $I_T$ and the remainder of the current to tip electrode 36 is less than or equal to approximately 20% of $I_T$. In other words, only approximately 20% of the induced current is delivered via tip electrode 36, which results in a reduction of unintended heat being transferred from tip electrode 36 to the tissue around the tip electrode 36. However, the amount of current that is redirected away from tip electrode 38 may be smaller than or greater that 80% of $I_T$ depending on the construction of electrode assembly 200, e.g., based on the surface area of tip electrode 36, the surface area of ring electrode 38, the size of coupler 217, the thickness of insulating layer 204 of coupler 217, the material from which electrodes 36, 38 or coupler 217 are constructed and the like.

Moreover, because ring electrode 38 has a large surface area relative to tip electrode 36, the current $I_T$ is spread over a larger total surface area resulting in a lower current density and less heating of the myocardial tissue. Instead, ring electrode 38 passes a large portion of the high frequency current into the blood stream contacting ring electrode 38 rather than through tip electrode 36 and into the myocardium tissue. In this manner, the amount of unintended heat being transferred from tip electrode 36 to the tissue around the tip electrode 36 is significantly reduced.

During pacing therapy, $I_T$ represents the pacing current generated by a pulse generator within IMD 14. At low frequencies (e.g., ~1 kHz for pacing signals) or direct current (DC) application capacitor $C_c$ acts substantially like an open circuit to a constant voltage across its terminals due to the small capacitance of $C_c$ compared to $C_t$. A majority of the pacing current therefore flows to tip electrode 36 and negligible or no current passes through the conductive coupler 217 to ring electrode 38. Thus, during delivery of pacing therapy, $I_r$ is very small compared to $I_T$, e.g., less than 1%. If the coupler-to-ring capacitance is approximately 500 pF, for example, only approximately 0.02% of the low frequency pacing current is redirected to ring electrode 38.

In sum, tip electrode 36 and conductive coupler 217 cooperate to serve as a high-pass filter, allowing low frequency signals to pass to tip electrode 36 and redirect high frequency signals to conductive coupler 217 and ultimately to ring electrode 36. In this manner, electrode assembly 200 reduces the effect of high frequency signals while not interfering with delivery of therapy. As described above, electrode assembly 200 is constructed to redirect at least a portion of the current from high frequency signals away from tip electrode 36 while only redirecting a small or negligible amount of current away from tip electrode 36 during low frequency therapy.

Figure 8:
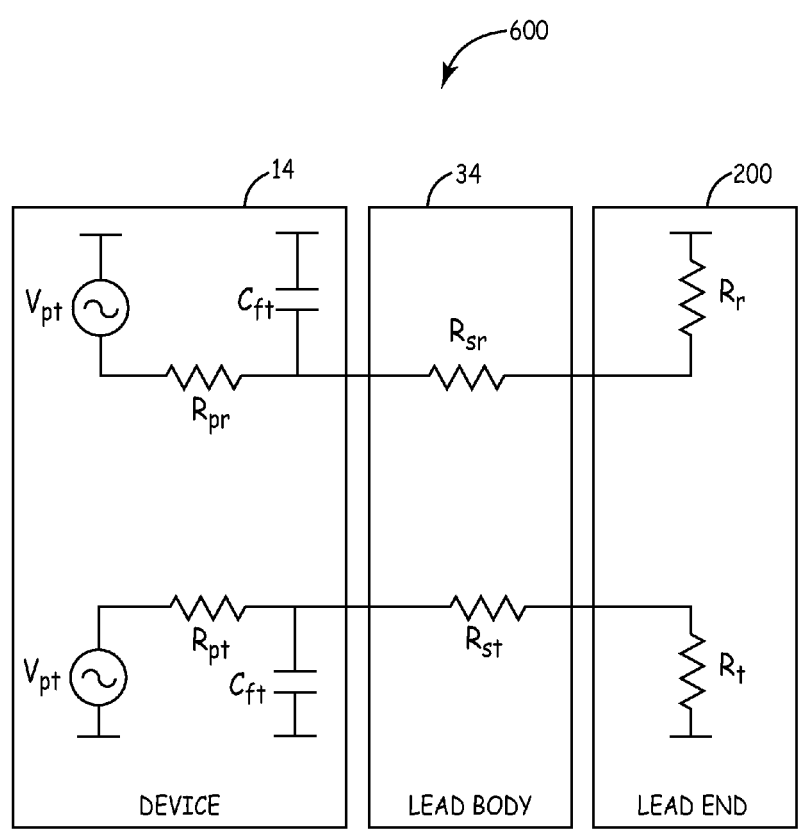
FIG. 8 depicts a circuit diagram illustrating another example circuit representing medical system during conventional pacing therapy.

FIG. 8 depicts a circuit diagram 600 illustrating another example circuit representing medical system 13 during conventional pacing therapy. If a patient's heart requires pacing from the IMD 14, pacing currents from the low frequency voltage sources $V_{pt}$ and/or $V_{pr}$ passes from the IMD 14 to the tip electrode 36, as shown in a circuit diagram 600 depicted in FIG. 8. Circuit diagram 600 extends from the IMD 14, the lead body 34, to an end of the lead assemblies 15. Voltage sources $V_{pt}$ and $V_{pr}$ for the tip and ring electrodes 36, 38 are used to represent or model the low frequency pacing signals from IMD 14. IMD 14 includes resistance $R_{pt}$ which relates to pacing to tip electrode 36, and a capacitance of a feed through $C_{ft}$. IMD 14 also includes resistance $R_{pr}$ which relates to pacing to ring electrode 38, and a capacitance related to a feed through $C_{ft}$. Lead body 34 includes resistance $R_{st}$ which is series resistance in the conductor of the lead body 34 connected to the tip electrode 36 whereas resistance $R_{sr}$ is series resistance of the wire connected to the ring electrode 38. Specifically, negligible or no pacing current passes through the coupler 217 because, under a low frequency or DC application, $C_c$ acts like an open circuit to a low frequency voltage across its terminals. Pacing current passes to the patient's tissue represented by the resistances $R_t$, $R_r$, and $R_{tr}$.

Figure 9:
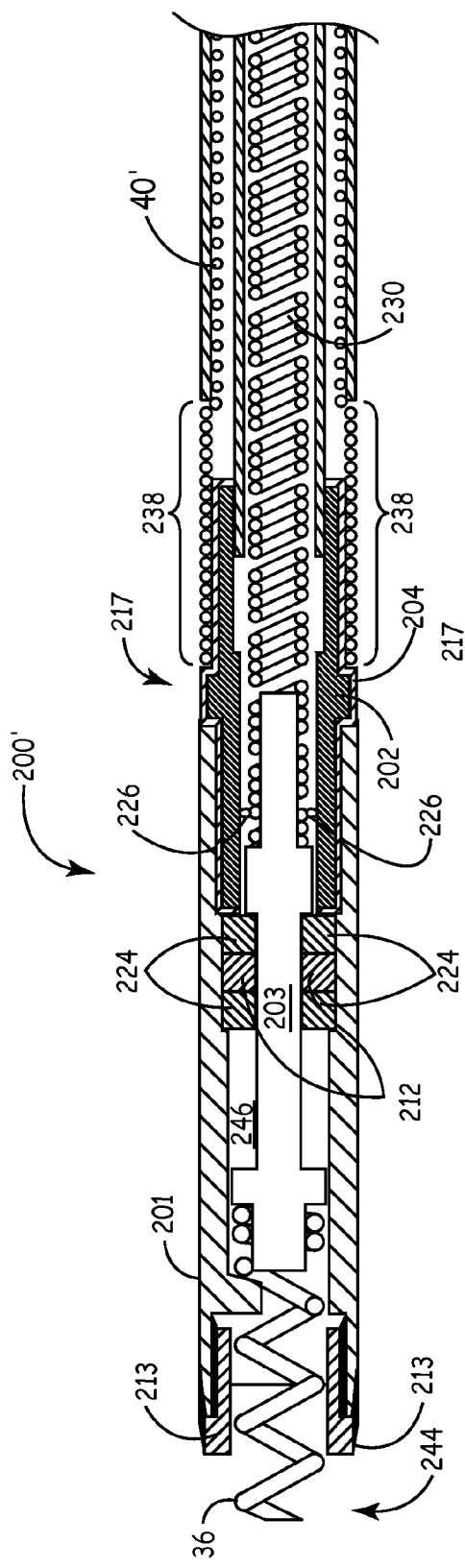
FIG. 9 is a schematic diagram illustrating another example electrode assembly.

FIG. 9 is a schematic diagram illustrating another example electrode assembly 200'. Electrode assembly 200' conforms substantially to electrode assembly 200 of FIGS. 4A-4C except that electrode assembly 200' includes a coil electrode 238 in place of ring electrode 38. Coil electrode 238 may be formed from a coiled conductor, such as coiled conductor 40', that extends along the length of lead body 34. Coil electrode 238 may, for example, be used as a sensing electrode or as a therapy electrode for delivery of defibrillation therapy.

As illustrated in FIG. 9, coiled conductor 40' may be located within a lumen defined by lead body 34 along a majority of the length of lead body and be located outside the lumen of lead body 34 at the distal end such that coiled conductor 40' is exposed to tissue and/or bodily fluids of patient 12. In this manner, coil electrode 238 is formed by the portion of coiled conductor 40 located outside of lead body 34.

In this case, conductive coupler 217 and defibrillation electrode 238 may be viewed as a capacitor with defibrillation electrode 238 being a first capacitive plate, a portion of conductive coupler 217 as a second capacitive plate, and the insulating material 204 being the dielectric between the two plates. At low frequencies and DC (e.g., during delivery of stimulation therapy), the capacitive coupling between conductive coupler 217 and defibrillation electrode 238 presents a high impedance allowing little current to be redirected to defibrillation electrode 238. However, at high frequencies (e.g., during an MRI scan) the capacitive coupling between conductive coupler 217 and defibrillation electrode 238 presents a low impedance, resulting in a significant amount of the induced current or energy being redirected to defibrillation electrode 238. As such, electrode assembly 200 redirects current from high frequency signals away from tip electrode 36 but does not significantly interfere with delivery of therapy (e.g., pacing pulses).

Figure 10:
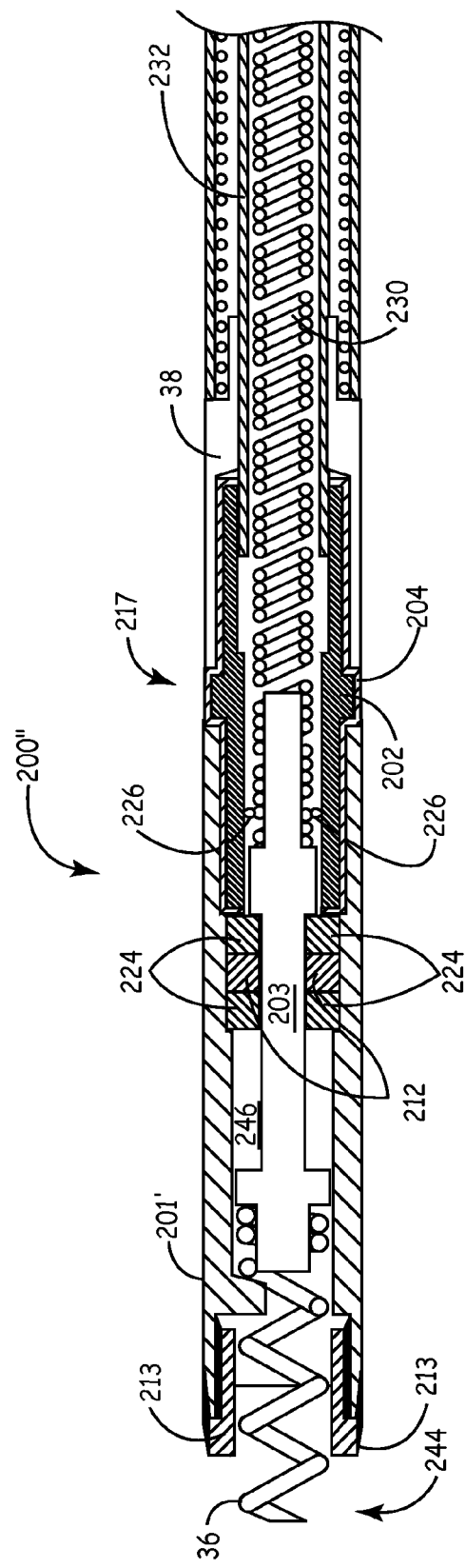
FIG. 10 is a schematic diagram illustrating another example electrode assembly.
Figure 14:
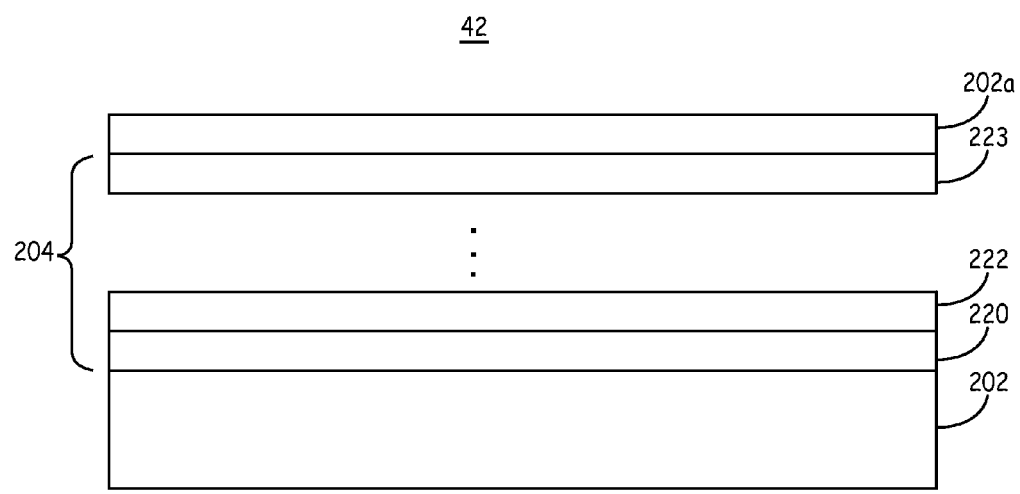
FIG. 14 depicts a material that can be used for forming a coupler or sleeve head for the electrode assembly.

FIG. 10 is a schematic diagram illustrating another example electrode assembly 200". Electrode assembly 200" conforms substantially to electrode assembly 200 of FIGS. 4A-4C except sleeve head 201' of electrode assembly 200" is made from an electrically conductive material instead of a non-conductive material. Sleeve head 201' may be formed in a similar manner to conductive coupler 217. For example, sleeve head 201' may be formed from an electrically conductive material with an insulative or dielectric layer wrapped or introduced around an outer diameter of the conductive material, as illustrated in FIG. 6 or 14.

Sleeve head 201' may be in electrical contact with conductive coupler 217 such that a portion of the current is redirected from electrode shaft 203 or tip conductor 230 to conductive coupler 217 and then a portion of the current redirected to the coupler 217 is passed to conductive sleeve head 201' while the remainder of the current is passed to ring electrode 38. In another embodiment, sleeve head 201' may not be in electrical contact with conductive coupler 217. Instead, sleeve head 201' may be in electrical contact with electrode shaft 203 via a coupling mechanism. For example, sleeve head 201' may be in electrical contact with electrode shaft via a conductive sealer 212, one or more conductive rings 224, a spring clip or via another coupling mechanism. Conductive sealer 212 and conductive rings 224 are described in more detail with respect to FIGS. 13A-13D. In still other instances, sleeve head 201' may electrically contact both conductive coupler 217 and electrode shaft 203. In any case, coupler 217 is used in combination with sleeve head 201' to redirect induced current away from tip electrode 36.

In a further embodiment, sleeve head 201' may be in electrical contact with electrode shaft 203 and conductive coupler 217 may be in electrical contact with sleeve head 201' and not be in electrical contact with tip conductor 230 or electrode shaft 203. Instead, a portion of the induced current is redirected to sleeve head 201' where a first portion is dissipated and a second portion is passed to conductive coupler 217 and ultimately to ring electrode 38 where it is dissipated. The embodiments described above that utilize a conductive sleeve head 201' may be used in conjunction with other electrodes, such as with an electrode assembly that includes a defibrillation electrode 238 in place of or in addition to ring electrode 38.

Utilizing conductive sleeve head 201' in conjunction with ring electrode 38 to dissipate the induced current may not only provide additional surface area over which the current may be dissipated, but it may also provide electrode assembly 200 with an overall impedance that does not match that of tip conductor 230. As such, a portion of the current induced in tip conductor 230 by the high frequency signals may be reflected back toward device 14. The characteristics of tip conductor 230, e.g., pitch, radius, number of turns, number of filars, or the like, may also be changed to achieve a desired impedance mismatch. Such a technique may be used in any of the embodiments described herein.

Figure 11:
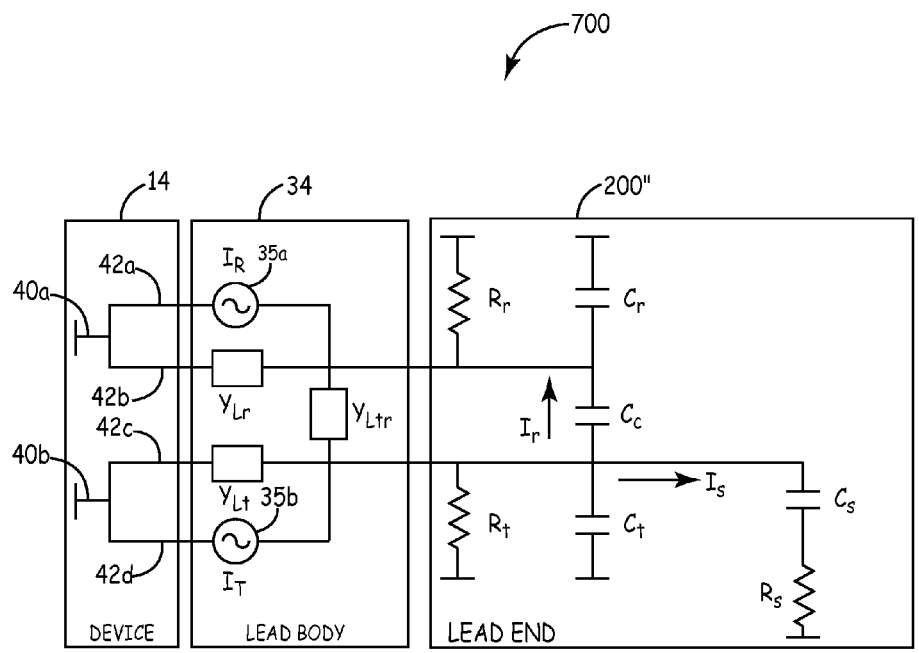
FIG. 11 is a schematic drawing illustrating a circuit diagram representing an example medical system having the electrode assembly depicted in FIG. 10.

FIG. 11 is a schematic drawing illustrating a circuit diagram 700 representing an example medical system 13 having electrode assembly 200" depicted in FIG. 10. Circuit diagram 700 is substantially similar to circuit diagram 500 of FIG. 7 except circuit diagram 700 includes elements resistance $R_s$ and capacitance $C_s$ that represent the electrical characteristics of sleeve head 201'.

Circuit diagram 700 redirects a portion of induced current $I_T$ away from the tip electrode 36 through the coupler 217 and to ring electrode 38, represented as $I_r$. Additionally, a portion of the induced current $I_T$ is redirected away from tip electrode 36 through sleeve head 201', which is represented as elements resistance $R_s$ and capacitance $C_s$. The current redirected through sleeve head 201' is represented as $I_s$. The amount of current redirected away from tip electrode (e.g., $I_r+I_s$) may be a large portion of the induced current $I_T$. In one example, $I_r+I_s$ may be at least 80% of $I_T$. Thus, capacitance, $C_c$, representing coupler 217, is used in combination with $C_s$ to redirect a portion of the induced current $I_T$ from tip electrode 36 to the ring electrode 38 and to the sleeve head 201'. $C_c$, $C_s$, and $R_s$ can be adjusted to optimize the amount of redirected portion of the induced current $I_T$.

In the example illustrated in FIG. 11, sleeve head 201' in electrical contact with tip conductor 230, electrode shaft 203 or tip electrode 36. In other words, sleeve head 201' is not in electrical contact with conductive coupler 217. Instead, sleeve head 201' may be in electrical contact with electrode shaft 203 via a coupling mechanism, e.g., via conductive sealer 212, one or more conductive rings 224, a spring clip or another coupling mechanism.

As described above with respect to FIG. 7, the induced current $I_T$ from exposure to a high frequency signal (e.g., from an MRI device 16) is formed in the lead body 34. A large portion of the induced current $I_T$ is redirected from the tip electrode 36 to either the ring electrode $R_r$, $C_r$ through coupler $C_c$ or to sleeve head 201' $R_s$, $C_s$. If a patient's heart requires pacing from the IMD 14, a current from the low frequency source passes from the IMD to the tip electrode 36. Specifically, negligible or no current pacing current passes through the coupler 217 or sleeve head 201' because, under a low frequency or direct current (DC) application, coupler 217 and sleeve head 201 act substantially like an open circuit to a constant voltage across its terminals. The pacing current passes to the patient's tissue through the tip electrode resistances $R_t$ and $C_t$, and through tissue/bodily fluid back to ring electrode $R_r$ and $C_r$.

Figure 12:
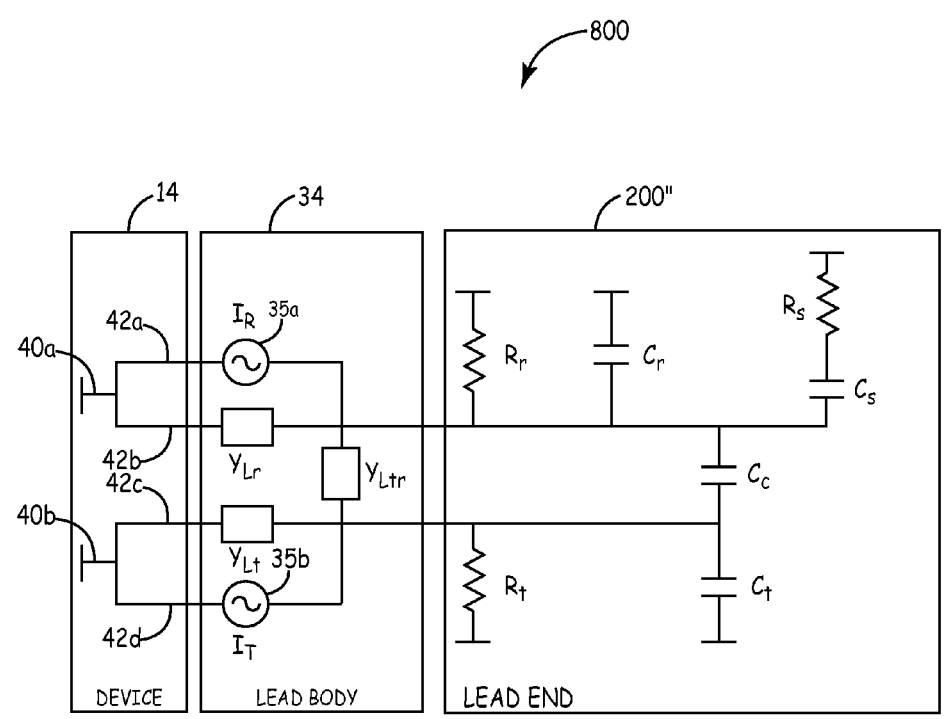
FIG. 12 is a schematic diagram illustrating another circuit diagram representing medical system having electrode assembly depicted in FIG. 11.
Figure 13A:
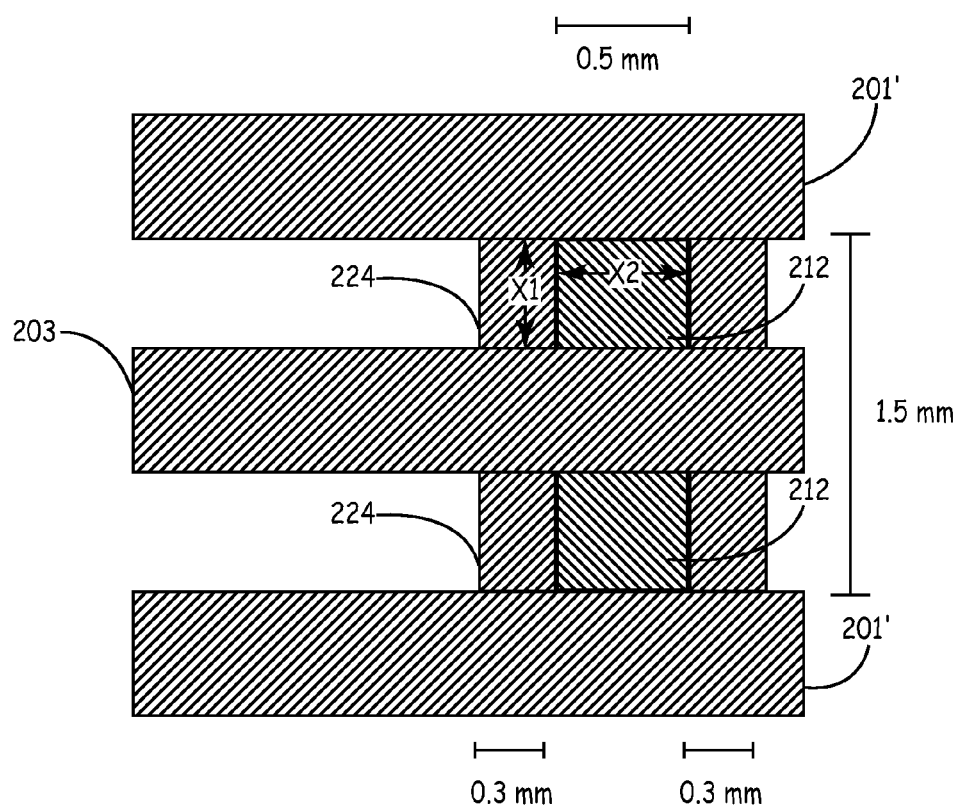
FIGS. 13A-13D are schematic diagrams depicting various views of a conductive sealer and conductive rings of an electrode assembly.
Figure 13B:
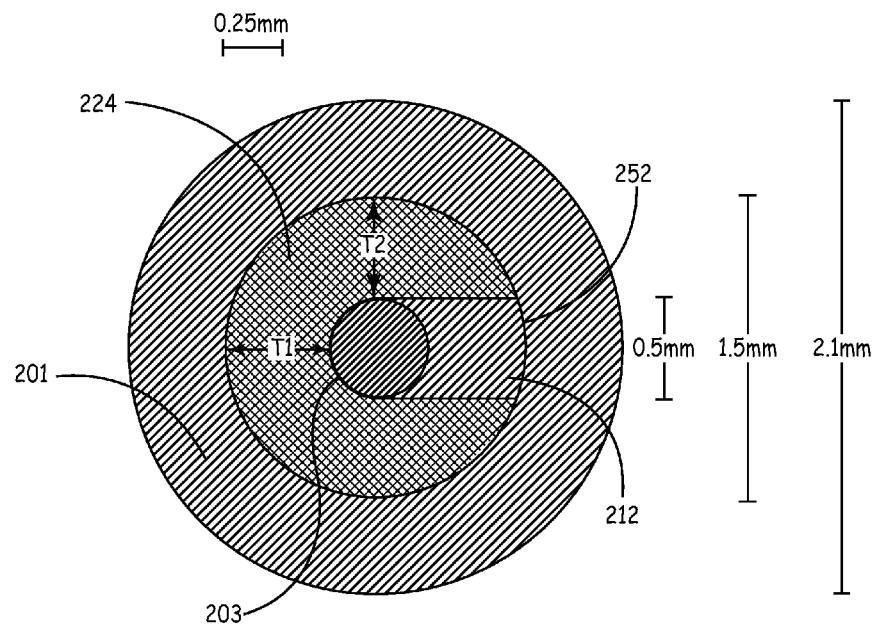
Figure 13C:
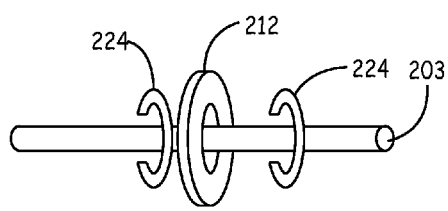
Figure 13D:
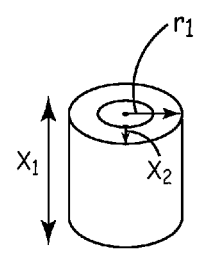

FIG. 12 is a schematic diagram illustrating another circuit diagram 800 representing medical system 13 having electrode assembly 200" depicted in FIG. 11. Circuit diagram 800 is substantially similar to circuit diagram 700 of FIG. 11 except circuit diagram 800 represents sleeve head 201' as being coupled to the tip electrode 36 through conductive coupler 217 instead of via a separate coupling mechanism. Thus, the elements representing sleeve head 201' are in series with $C_c$ instead of being in parallel with $C_c$ as depicted in FIG. 11.

Figure 15:
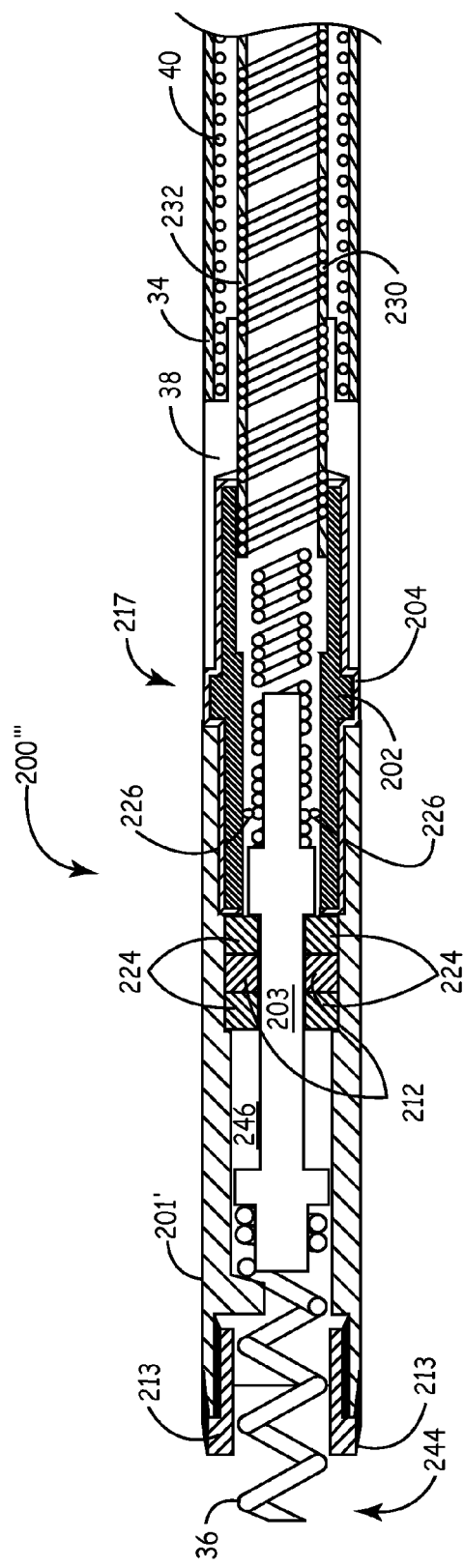
FIG. 15 is a schematic diagram illustrating yet another embodiment of an electrode assembly 200'''.

FIG. 15 is a schematic diagram illustrating yet another embodiment of an electrode assembly 200''' in which tip conductor 230 is embedded or buried into a polymer 232 to assist in redirecting a portion of induced current away from tip electrode 36 to ring electrode 38. In this embodiment, electrode assembly 200''' is the same as described above except that coil 230 assists coupler 217 in redirecting induced current. In other words, tip conductor 230 is also capacitively coupled to a second electrode (e.g., ring electrode 38 or coil electrode 238) to assist coupler 217 in redirecting induced current to ring electrode 38. In this manner, a first portion of the redirected current is redirected from tip electrode 36 via the capacitive coupling between the tip conductor 230 and the second electrode and a second portion of the redirected current is redirected from the first electrode to the second electrode via the conductive elongated coupler.

Numerous other embodiments related to electrode assembly 200 can be implemented through the use of the material depicted in FIG. 14 in place of the material depicted in FIG. 6. The material depicted in FIG. 14 is the same as FIG. 6 except another conductive material 202a is placed directly on top of insulative material 204. In this embodiment, conductive material 202a is directly exposed to tissue of the heart 42.

It is understood that the present disclosure is not limited for use in pacemakers, cardioverters of defibrillators. Other uses of the leads described herein may include uses in patient monitoring devices, or devices that integrate monitoring and stimulation features. In those cases, the leads may include sensors disposed on distal ends of the respective lead for sensing patient conditions.

The leads described herein may be used with a neurological device such as a deep-brain stimulation device or a spinal cord stimulation device. In those cases, the leads may be stereotactically probed into the brain to position electrodes for deep brain stimulation, or into the spine for spinal stimulation. In other applications, the leads described herein may provide muscular stimulation therapy, gastric system stimulation, nerve stimulation, lower colon stimulation, drug or beneficial agent dispensing, recording or monitoring, gene therapy, or the like. In short, the leads described herein may find useful applications in a wide variety medical devices that implement leads and circuitry coupled to the leads.

Various embodiments of the disclosure have been described. These and other embodiments are within the scope of the following claims. For example, electrode 36 may include variously shaped electrodes such as ring shaped or other suitable shapes. Additionally, skilled artisans appreciate that other dimensions may be used for the mechanical and electrical elements described herein. It is also expected that the teachings herein, while described relative to a bipolar lead, can also be applied to a unipolar lead.

The invention claimed is:

1. An electrode assembly for a medical electrical lead, the electrode assembly comprising:
   a first electrode located near a distal end of the electrode assembly;
   an electrode shaft having a proximal end and a distal end, wherein the distal end of the electrode shaft is configured to mechanically couple to the first electrode and the proximal end of the electrode shaft is configured to mechanically couple to a first conductor of the electrical lead;
   a second electrode located near a proximal end of the electrode assembly;
   a conductive elongated coupler configured to electrically couple to at least one of the first electrode, the electrode shaft or the first conductor and arranged such that at least a portion of the conductive elongated coupler is adjacent to at least a portion of the second electrode; and
   an insulation layer separating the portion of the conductive elongated coupler that is adjacent to the portion of the second electrode such that the portion of the conductive elongated coupler is capacitively coupled to the portion of the second electrode such that at least a portion of current induced by a high frequency signal is redirected from the first electrode to the second electrode.

2. The electrode assembly of claim 1, wherein the conductive elongated coupler includes:
   a conductive element having a proximal end and a distal end, wherein the conductive element is electrically connected to the first electrode; and
   wherein the insulation layer covers at least a portion of an outer surface of the conductive element.

3. The electrode assembly of claim 1, wherein the insulation layer covers any portion of the conductive elongated coupler that will be exposed to body fluids.

4. The electrode assembly of claim 2, wherein the insulation layer is less than approximately one millimeter thick.

5. The electrode assembly of claim 1, wherein the first electrode is a tip electrode and the second electrode is a ring electrode.

6. The electrode assembly of claim 1, wherein the first electrode is a tip electrode and the second electrode is a coil electrode.

7. The electrode assembly of claim 1, further comprising a sleeve head that includes:
a conductive element having a proximal end and a distal end, wherein the conductive element of the sleeve head electrically couples to the first electrode; and
a dielectric coating introduced over at least a portion of the conductive element that will be exposed to body fluids.

8. The electrode assembly of claim 7, wherein the conductive element of the sleeve head electrically couples to the first electrode via the conductive elongated coupler.

9. The electrode assembly of claim 7, wherein the conductive element of the sleeve head electrically couples to the first electrode via a coupling mechanism that is separate from the conductive elongated coupler.

10. The electrode assembly of claim 9, wherein the sleeve head does not electrically contact the conductive elongated coupler.

11. The electrode assembly of claim 1, wherein the second electrode is configured to mechanically couple to a second conductor of the electrical lead.

12. The electrode assembly of claim 1, further comprising a conductive connector mechanism to electrically couple the conductive elongated coupler and one of the first electrode, the electrode shaft or the first conductor.

13. The electrode assembly of claim 1, wherein the second electrode is a ring electrode having a cylindrical shape and the portion of the elongated conductive coupler adjacent to the ring electrode has a cylindrical shape.

14. A medical electrical lead comprising:
a lead body having a proximal end configured to couple to an implantable medical device and a distal end;
a first conductor that extends from the proximal end of the lead body to the distal end of the lead body; and
an electrode assembly located at the distal end of the lead body, the electrode assembly including:
a first electrode located near a distal end of the electrode assembly;
an electrode shaft having a proximal end and a distal end, wherein the distal end of the electrode shaft is configured to mechanically couple to the first electrode and the proximal end of the electrode shaft is configured to mechanically couple to the first conductor of the electrical lead;
a second electrode located near a proximal end of the electrode assembly;
a conductive elongated coupler configured to electrically couple to at least one of the first electrode, the electrode shaft or the first conductor and arranged such that at least a portion of the conductive elongated coupler is adjacent to at least a portion of the second electrode; and
an insulation layer separating the portion of the conductive elongated coupler that is adjacent to the portion of the second electrode such that the portion of the conductive elongated coupler is capacitively coupled to the portion of the second electrode such that at least a portion of current induced by a high frequency signal is redirected from the first electrode to the second electrode.

15. The medical electrical lead of claim 14, wherein the conductive elongated coupler includes:
a conductive element having a proximal end and a distal end, wherein the conductive element is electrically connected to the first electrode; and
wherein the insulation layer covers at least a portion of an outer surface of the conductive element that will be exposed to body fluids.

16. The electrode assembly of claim 15, wherein the insulation layer is less than approximately one hundred (100) micrometers thick.

17. The medical electrical lead of claim 14, wherein the first electrode is a tip electrode and the second electrode is one of a ring electrode and a coil electrode.

18. The medical electrical lead of claim 14, further comprising a sleeve head that includes:
a conductive element having a proximal end and a distal end, wherein the conductive element of the sleeve head electrically couples to the first electrode; and a dielectric coating introduced over at least a portion of the conductive element that will be exposed to body fluids.

19. The medical electrical lead of claim 18, wherein the conductive element of the sleeve head electrically couples to the first electrode via the conductive elongated coupler.

20. The medical electrical lead of claim 18, wherein the conductive element of the sleeve head electrically couples to the first electrode via a coupling mechanism that is separate from the conductive elongated coupler.

21. The medical electrical lead of claim 14, further comprising a second conductor that is mechanically and electrically coupled to the second electrode.

22. The medical electrical lead of claim 14, wherein the first conductor is embedded within a polymer and capacitively coupled to the second electrode such that a first portion of the redirected current is redirected from the first electrode via the capacitive coupling between the first conductor and the second electrode and a second portion of the redirected current is redirected from the first electrode via the conductive elongated coupler.

23. The medical electrical lead of claim 14, wherein the second electrode is a ring electrode having a cylindrical shape and the portion of the elongated conductive coupler adjacent to the ring electrode has a cylindrical shape.

24. A medical electrical lead comprising:
a lead body having a proximal end configured to couple to an implantable medical device and a distal end;
a first conductor that extends from the proximal end of the lead body to the distal end of the lead body; and
an electrode assembly located at the distal end of the lead body, the electrode assembly including:
a first electrode;
an electrode shaft having a proximal end and a distal end, wherein the distal end of the electrode shaft is mechanically coupled to the first electrode and the proximal end of the electrode shaft is mechanically coupled to the first conductor of the electrical lead;
a second electrode located toward the proximal end of the lead body compared to the first electrode;
a conductive elongated coupler configured to electrically couple to at least one of the first electrode, the electrode shaft or the first conductor and arranged such that at least a portion of the conductive elongated coupler is adjacent to at least a portion of the second electrode; and
an insulation layer separating the portion of the conductive elongated coupler that is adjacent to the portion of the second electrode such that at least a portion of current induced by a high frequency signal on the first conductor is redirected from the first conductor to the conductive elongated coupler via the electrical coupling and from the portion of the conductive elongated coupler that is adjacent to the portion of the second electrode through the insulation layer to the second electrode.

* * * * *